US011739147B2

(12) United States Patent
Chen et al.

(10) Patent No.: US 11,739,147 B2
(45) Date of Patent: Aug. 29, 2023

(54) ANTIBODIES BINDING SIGLEC15 AND USES THEREOF

(71) Applicant: Biosion, Inc. Biosion Inc., Jiangsu (CN)

(72) Inventors: Mingjiu Chen, Jiangsu (CN); Shukai Xia, Jiangsu (CN)

(73) Assignee: Biosion Inc., Jiangsu (CN)

( * ) Notice: Subject to any disclaimer, the term of this patent is extended or adjusted under 35 U.S.C. 154(b) by 0 days.

(21) Appl. No.: 17/935,815

(22) Filed: Sep. 27, 2022

(65) Prior Publication Data

US 2023/0106715 A1 Apr. 6, 2023

Related U.S. Application Data

(63) Continuation of application No. PCT/CN2021/083194, filed on Mar. 26, 2021.

(60) Provisional application No. 63/000,566, filed on Mar. 27, 2020.

(51) Int. Cl.
 *C07K 16/28* (2006.01)

(52) U.S. Cl.
 CPC ...... *C07K 16/2803* (2013.01); *C07K 2317/14* (2013.01); *C07K 2317/24* (2013.01); *C07K 2317/52* (2013.01); *C07K 2317/565* (2013.01); *C07K 2317/92* (2013.01)

(58) Field of Classification Search
 CPC .................................................. C07K 16/2896
 USPC ........................................... 424/133.1, 138.1
 See application file for complete search history.

(56) References Cited

U.S. PATENT DOCUMENTS

| | | | |
|---|---|---|---|
| 8,741,289 B2 | 6/2014 | Tremblay et al. | |
| 9,447,192 B2 | 9/2016 | Elvin et al. | |
| 2015/0125470 A1 | 5/2015 | Hiruma et al. | |
| 2019/0202912 A1 | 7/2019 | Liu et al. | |

FOREIGN PATENT DOCUMENTS

| | | | |
|---|---|---|---|
| JP | 2007020403 A | | 2/2007 |
| WO | WO-2011041894 A1 | | 4/2011 |
| WO | WO-2017083354 A1 | | 5/2017 |
| WO | WO-2018057735 A1 | | 3/2018 |
| WO | WO2021/190622 | * | 9/2021 |

OTHER PUBLICATIONS

Peng et al (Cancer Research, (Jun. 2022) vol. 82, No. 12, Supp. Supplement. Abstract No. 5522. Meeting Info: American Association for Cancer Research Annual Meeting, ACCR 2020. New Orleans, LA, United States. Apr. 8, 2022-Apr. 13, 2022).*
Antibody System (CD33L, BSI-060T, DHK13703; datahseet pp. 1-2 (May 1, 2023)).*
Angata et al., "Siglec-15: an immune system Siglec conserved throughout vertebrate evolution." Glycobiology. 2007;17(8):838-46.
Angata, "Siglec-15: a potential regulator of osteoporosis, cancer, and infectious diseases." J Biomed Sci. 2020;27(1):10.
Hiruma et al., "Impaired osteoclast differentiation and function and mild osteopetrosis development in Siglec-15-deficient mice." Bone. Mar. 2013;53(1):87-93.
Hiruma et al., "Siglec-15, a member of the sialic acid-binding lectin, is a novel regulator for osteoclast differentiation." Biochem Biophys Res Commun. 2011;409(3):424-9.
Häuselmann et al., "Altered tumor-cell glycosylation promotes metastasis." Front Oncol. 2014;4:28.
Kang et al., "The diverse functions of Siglec-15 in bone remodeling and antitumor responses." Pharmacol Res. May 2020;155:104728.
PCT International Search Report and Written Opinion from PCT/CN2021/083194, dated Jun. 9, 2021.
Sato et al., "Siglec-15-targeting therapy increases bone mass in rats without impairing skeletal growth." Bone. 2018;116:172-180.
Stuible et al., "Mechanism and function of monoclonal antibodies targeting siglec-15 for therapeutic inhibition of osteoclastic bone resorption." J Biol Chem. 2014;289(10):6498-6512.
Sun et al., "Siglec-15 as an Emerging Target for Next-generation Cancer Immunotherapy." Clin Cancer Res. 2021;27(3):680-688.
Takamiya et al., "The interaction between Siglec-15 and tumor-associated sialyl-Tn antigen enhances TGF-ß secretion from monocytes/macrophages through the DAP12-Syk pathway." Glycobiology. 2013;23(2):178-87.
Wang et al., "Siglec-15 as an immune suppressor and potential target for normalization cancer immunotherapy," Nat Med. Apr. 2019;25(4):656-666.

* cited by examiner

*Primary Examiner* — Lynn A Bristol
(74) *Attorney, Agent, or Firm* — Dechert LLP; Andrew T. Wilkins; Kayla L. Metzger

(57) ABSTRACT

An isolated monoclonal antibody that specifically binds human Siglec15, or an antigen-binding portion thereof. A nucleic acid molecule encoding the antibody or antigen-binding portion thereof, an expression vector, a host cell and a method for expressing the antibody or antigen-binding portion thereof are also provided. The present disclosure further provides an immunoconjugate, a bispecific molecule, a chimeric antigen receptor, an oncolytic virus and a pharmaceutical composition comprising the antibody or antigen-binding portion thereof, as well as a treatment method using the same.

30 Claims, 14 Drawing Sheets

Specification includes a Sequence Listing.

ANTIBODIES BINDING SIGLEC15 AND USES THEREOF

RELATED APPLICATIONS AND INCORPORATION BY REFERENCE

This application is a continuation of PCT international application PCT/CN2021/083194 (published as WO 2021/190622), filed Mar. 26, 2021, which claims priority to U.S. provisional patent application Ser. No. 63/000,566, filed on Mar. 27, 2020.

The foregoing applications, and all documents cited therein or during their prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any GenBank® sequences mentioned in this disclosure are incorporated by reference with the GenBank® sequence to be that of the earliest effective filing date of this disclosure.

SEQUENCE LISTING

The content of the electronically submitted Sequence Listing XML (Name: 193623_SL; Size: 69,414 bytes; Created: Apr. 19, 2023) is herein incorporated by reference in its entirety.

FIELD OF THE INVENTION

The present disclosure relates generally to an isolated monoclonal antibody, such as a fully human, mouse, chimeric or humanized monoclonal antibody, or an antigen-binding portion thereof, that specifically binds to Siglec15 with high affinity and functionality. A nucleic acid molecule encoding the antibody or antigen-binding portion thereof, an expression vector, a host cell and a method for expressing the antibody or antigen-binding portion thereof are also provided. The present disclosure further provides an immunoconjugate, a bispecific molecule, a chimeric antigen receptor, an oncolytic virus, and a pharmaceutical composition comprising the antibody or antigen-binding portion thereof, as well as a diagnostic and treatment method using an anti-Siglec15 antibody of the disclosure.

BACKGROUND OF THE INVENTION

Immunotherapy is a revolutionary therapeutic approach that boosts the immune system to fight diseases such as cancer. It is applicable to many indications and offers a lesser high-grade toxicity compared with other stand therapies. The PD-1/PD-L1 pathway is a hot target in tumor immunotherapy, and several inhibitors of either PD-1 or PD-L1 have been clinically approved, such as the anti-PD-1 antibodies Opdivo® (nivolumab) and Keytruda® (pembrolizumab), and the anti-PD-L1 antibody Tecentriq® (atezolizumab). However, a subset of patients does not respond to such treatments. As revealed by a recent study, Siglec15 targeting may be a complementary approach for cancer patients unresponsive to PD-1/PD-L1 targeting therapies (Jun Wang et al., (2019) Nature Medicine 25:656-666).

Siglec15 is a member of Siglec family with a sialic acid-binding immunoglobulin-type lectin structure. It contains two extracellular immunoglobulin-like domains, a transmembrane domain with a lysine residue that is essential for the interaction with adapter protein DAP12, and a cytoplasmic tail (Takashi Angata et al., (2007) Glycobiology 17(8):838-846).

Siglec15 is expressed on osteoclasts, and plays a role in osteoclast differentiation and bone remodeling (Hiruma Y et al., (2011) Biochemical and Biophysical Research Communications 409(3):424-429; Takashi Angata (2020) Journal of Biomedical Science 27:10). The administration of anti-Siglec15 antibodies inhibited osteoclastic bone resorption and increased bone mass in rodent models (Stuible M et al., (2014) Journal of Biological Chemistry 289(10):6498-6512; Sato D et al., (2018) Bone 116:172-180).

Siglec15 is also expressed on tumor-associated macrophages and preferentially recognizes the sialyl-Tn antigen, a tumor associated glycan structure. The co-culture of sialyl-Tn/− cancer cell line and M-CSF-induced human macrophages or Siglec15$^+$ myeloid cell line induced the production of transforming growth factor-β, which promoted epithelia-mesenchymal transition and metastasis of cancer cells (Takamiya R et al., (2013) Glycobiology 23(2):178-187). Lieping Cheng et al., recently discovered that Siglec15 is further expressed on tumor cells and/or tumor-associated stromal cells in clinical non-small cell lung cancer samples. They also found Siglec15 proteins suppressed T cell proliferation and activation, and the anti-Siglec15 antibodies reversed T cell suppression and attenuated cancer growth in vivo. As Siglec15 and PD-L1 are mutually exclusive in cancer tissues, Siglec15 may serve as a complementary therapeutic target and offers alternative treatment to patients that are refractory to PD-1/PD-L1 blockade, as mentioned above ((Jun Wang et al., (2019) supra). NC318, a humanized anti-Siglec15 antibody, has been clinically tested in patients with advanced solid tumors, including non-small cell lung cancer, ovarian cancer, melanoma, colorectal cancer, and breast cancer, and prolonged stabilization of disease was observed in 54% of the patients and objective response in 5.4% (Sun J et al., (2021) Clin Cancer Res. 27(3):680-688).

In view of Siglec15's engagement in bone remodeling, and tumor development, Siglect15 is definitely an emerging promising therapeutic target. Anti-Siglec15 antibodies with improved pharmaceutical characteristics are needed.

Citation or identification of any document in this application is not an admission that such document is available as prior art to the present invention.

SUMMARY OF THE INVENTION

The present disclosure provides an isolated mouse, chimeric, human or humanized monoclonal antibody, or an antigen-binding portion thereof, that binds to Siglec15 (e.g., the human Siglec15, and monkey Siglec15) and has comparable, if not higher, binding affinity/capacity to Siglec15 and blocking activity on Siglec15 binding to a ligand such as LRRC4C, as compared to prior art anti-Siglec15 antibodies such as Siglec15-ch5G9 (Nextcure). The antibody or antigen-binding portion thereof is capable of reversing Siglec15 mediated T cell suppression.

The antibody or antigen-binding portion thereof of the disclosure can be used for a variety of applications, including detection of the Siglec15 protein, and treatment and prevention of Siglec15 associated diseases, such as tumors and osteoporosis.

Accordingly, in one aspect, the disclosure pertains to an isolated monoclonal antibody (e.g., a human, mouse, chimeric or humanized antibody), or an antigen-binding portion thereof, that binds Siglec15, having i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 44 and 3, respectively; (2) SEQ ID NOs: 1, 45 and 3, respectively; (3) SEQ ID NOs: 1, 46 and 3, respectively; (4) SEQ ID NOs: 9, 10 and 11, respectively; or (5) SEQ ID NOs: 33, 34 and 35, respectively; and/or ii) a light chain variable region that may comprise a VL CDR1 region, a VL CDR2 region and a VL CDR3 region, wherein the VL CDR1 region, the VL CDR2 region, and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 4, 5 and 6, respectively; (2) SEQ ID NOs: 12, 13 and 14, respectively; or (3) SEQ ID NOs: 36, 37 and 38, respectively.

The antibody or antigen-binding portion thereof of the disclosure may comprise a heavy chain variable region that may comprise a VH CDR1 region, a VH CDR2 region and a VH CDR3 region, and a light chain variable region that may comprise a VL CDR1 region, a VL CDR2 region and a VL CDR3 region, wherein the VH CDR1 region, the VH CDR2 region, the VH CDR3 region, the VL CDR1 region, the VL CDR2 region, and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 44, 3, 4, 5 and 6, respectively; (2) SEQ ID NOs: 1, 45, 3, 4, 5 and 6, respectively; (3) SEQ ID NOs: 1, 46, 3, 4, 5 and 6, respectively; (4) SEQ ID NOs: 9, 10, 11, 12, 13 and 14, respectively; or (5) SEQ ID NOs: 33, 34, 35, 36, 37 and 38, respectively, wherein the antibody or antigen-binding fragment thereof binds to Siglec15.

The heavy chain variable region of the antibody or antigen-binding portion thereof of the disclosure may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 47, 48, 49, 15, 39, 40 or 41, wherein the antibody or antigen-binding fragment thereof binds to Siglec15. The amino acid sequence of SEQ ID NO: 47 may be encoded by the nucleotide sequence of SEQ ID NOs: 27, and the amino acid sequence of SEQ ID NO: 15 may be encoded by the nucleotide sequence of SEQ ID NO: 29.

The light chain variable region of the antibody or antigen-binding portion thereof of the disclosure may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 8, 16, 42 or 43, wherein the antibody or antigen-binding fragment thereof binds to Siglec15. The amino acid sequences of SEQ ID NO: 8 and 16 may be encoded by nucleotide sequences of SEQ ID NOs: 28 and 30.

The antibody or antigen-binding portion thereof of the disclosure may comprise a heavy chain variable region and a light chain variable region having amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 47 and 8, respectively; (2) SEQ ID NOs: 48 and 8, respectively; (3) SEQ ID NOs: 49 and 8, respectively; (4) SEQ ID NOs: 15 and 16, respectively; (5) SEQ ID NOs: 39 and 42, respectively; (6) SEQ ID NOs: 40 and 42, respectively; or (7) SEQ ID NOs: 41 and 43, respectively, wherein the antibody or antigen-binding fragment thereof binds to Siglec15.

The isolated monoclonal antibody, or the antigen-binding portion thereof, of the present disclosure may comprise a heavy chain and a light chain linked by disulfide bonds, the heavy chain may comprise a heavy chain variable region and a heavy chain constant region, the light chain may comprise a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region may comprise amino acid sequences described above, and the antibody or antigen-binding portion thereof binds to Siglec15. The heavy chain constant region may be a IgG1, IgG2 or IgG4 heavy chain constant region, e.g., human IgG1, IgG2 or IgG4 heavy chain constant region having the amino acid sequence set forth in e.g., SEQ ID NO.:17. The heavy chain constant region, such as the Fc fragment, may be engineered to have reduced or enhanced FcR binding affinity. The light chain constant region may be kappa constant region, e.g., human kappa constant region having the amino acid sequences set forth in e.g., SEQ ID NO.: 18. The amino acid sequences of SEQ ID NOs: 17 and 18 may be encoded by the nucleotide sequences of SEQ ID NOs: 31 and 32, respectively.

The antibody of the present disclosure in certain embodiments may comprise or consist of two heavy chains and two light chains, wherein each heavy chain may comprise the heavy chain constant region, heavy chain variable region or CDR sequences mentioned above, and each light chain may comprise the light chain constant region, light chain variable region or CDR sequences mentioned above, wherein the antibody binds to Siglec15. The antibody or antigen-binding portion thereof of the disclosure can be a full-length antibody, for example, of an IgG1, IgG2 or IgG4 isotype. The antibody or the antigen-binding portion thereof of the present disclosure in other embodiments may be a single chain variable fragment (scFv) antibody, or an antibody fragment, such as a Fab or F(ab')2 fragment.

The disclosure also provides a bispecific molecule that may comprise the antibody, or the antigen-binding portion thereof, of the disclosure, linked to a second functional moiety (e.g., a second antibody) having a different binding specificity than said antibody, or antigen-binding portion thereof. The disclosure also provides an immunoconjugate, such as an antibody-drug conjugate, that may comprise an antibody, or an antigen-binding portion thereof, of the disclosure, linked to a therapeutic agent, such as a cytotoxin. In another aspect, the antibody or the antigen binding portion thereof of the present disclosure can be made into part of a chimeric antigen receptor (CAR). Also provided is an immune cell that may comprise the antigen chimeric receptor, such as a T cell and a NK cell. The antibody or the antigen binding portion thereof of the present disclosure can also be encoded by or used in conjunction with an oncolytic virus.

Nucleic acid molecules encoding the antibody, or the antigen-binding portion thereof, of the disclosure are also encompassed by the disclosure, as well as expression vectors that may comprise such nucleic acids and host cells that may comprise such expression vectors. A method for preparing the anti-Siglec15 antibody or the antigen-binding portion thereof of the disclosure using the host cell is also provided, that may comprise steps of (i) expressing the antibody in the host cell and (ii) isolating the antibody from the host cell or its cell culture.

Compositions that may comprise the antibody, or the antigen-binding portion thereof, the immunoconjugate, the bispecific molecule, the oncolytic virus, the CAR, the CAR-T cell, the nucleic acid molecule, the expression vector or the host cells of the disclosure, and a pharmaceutically acceptable carrier, are also provided. In certain embodiments, the pharmaceutical composition may further contain a therapeutic agent such as an anti-cancer agent.

In yet another aspect, the disclosure provides a method of modulating an immune response in a subject comprising administering to the subject a therapeutically effective amount of the antibody or antigen-binding portion thereof, of the disclosure, or alternatively a nucleic acid molecule capable of expressing the same in the subject, such that the immune response in the subject is modulated. Preferably, the antibody or antigen-binding portion thereof of the disclosure enhances, stimulates or increases the immune response in the subject, e.g., by reversing Siglec15 mediated T cell suppression. In some embodiments, the method comprises administering a bispecific molecule, an immunoconjugate, a CAR-T cell, or an antibody-encoding or antibody-bearing oncolytic virus of the disclosure.

In yet another aspect, the disclosure provides a method of inhibiting bone loss or increasing boss mass in a subject comprising administering to the subject a therapeutically effective amount of the antibody, or antigen-binding portion thereof, of the disclosure, or alternatively a nucleic acid molecule capable of expressing the same.

In a further aspect, the disclosure provides a method of inhibiting tumor growth in a subject in need thereof, comprising administering to a subject a therapeutically effective amount of the antibody or antigen-binding portion thereof, of the disclosure, or alternatively a nucleic acid molecule capable of expressing the same in the subject. In some embodiments, the method comprises administering a bispecific molecule, an immunnoconjugate, a CAR-T cell, or an antibody-encoding or antibody-bearing oncolytic virus of the disclosure. The tumor may be a solid or non-solid tumor. In certain embodiments, the tumor is solid tumor, including, but not limited to, non-small cell lung cancer, ovarian cancer, melanoma, colorectal cancer, breast cancer (including triple-negative breast cancer), head and neck squamous cell carcinoma, endometrial cancer, and squamous cell carcinoma. In some embodiments, at least one additional anti-cancer antibody can be administered with the antibody, or an antigen-binding portion thereof, of the disclosure, such as an anti-VISTA antibody, an anti-PD-1 antibody, an anti-PD-L1 antibody, an anti-LAG-3 antibody, an anti-CTLA-4 antibody, an anti-TIM-3 antibody, an anti-STAT3 antibody, and/or an anti-ROR1 antibody. In yet another embodiment, an antibody, or an antigen-binding portion thereof, of the disclosure is administered with a cytokine (e.g., IL-2, IL-21, GM-CSF and/or IL-4), or a costimulatory antibody (e.g., an anti-CD137 and/or anti-GITR antibody). In another embodiment, an antibody, or an antigen-binding portion thereof, of the disclosure is administered with a chemotherapeutic agent, which may be a cytotoxic agent, such as epirubicin, oxaliplatin, and/or 5-fluorouracil (5-FU). The antibody or antigen-binding portion thereof of the present disclosure may be, for example, mouse, human, chimeric or humanized.

Other features and advantages of the instant disclosure will be apparent from the following detailed description and examples, which should not be construed as limiting. The contents of all references, GenBank® entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

(B), A2A6B1C2, A2G4C8G7 and A2H5F1A1 (C) to mouse Siglec15 in an indirect ELISA.

Figure 5A:
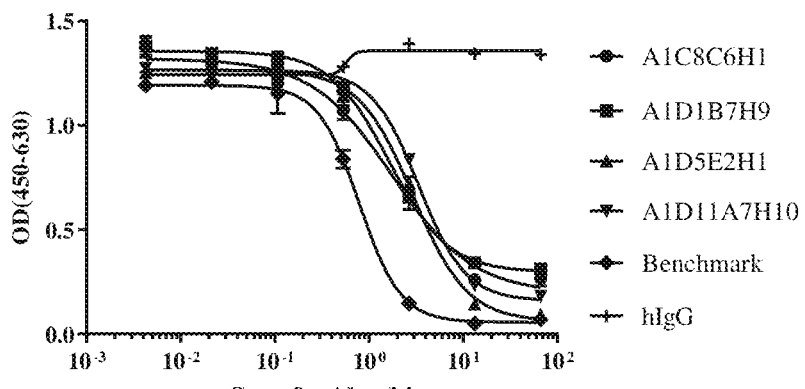
Figure 5B:
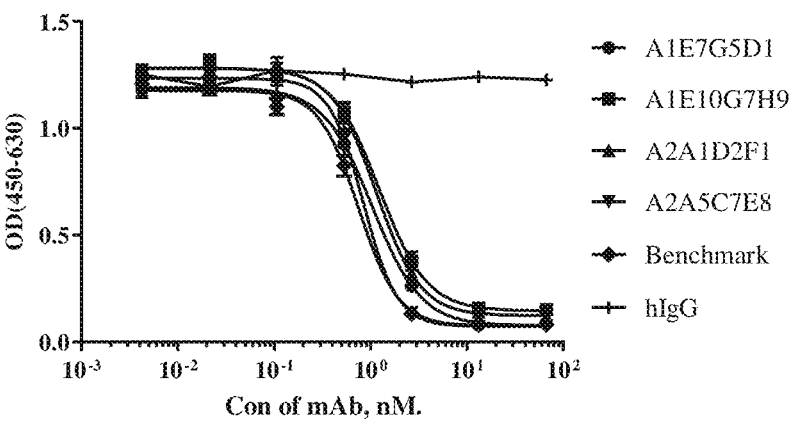
Figure 5C:
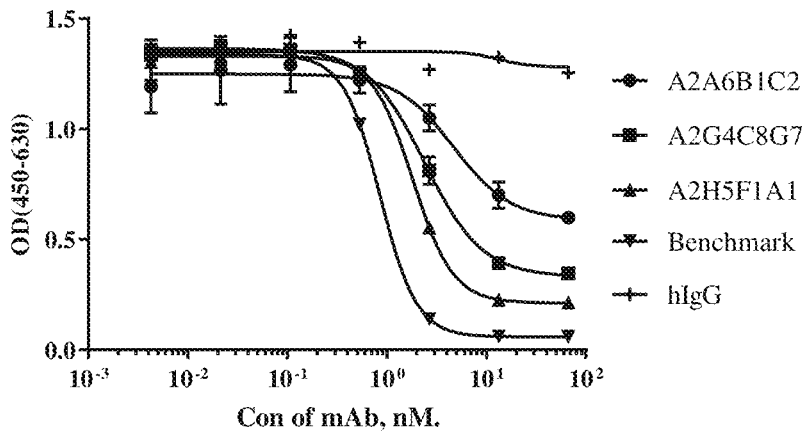

FIGS. 5A-5C show the abilities of antibodies A1C8C6H1, A1D1B7H9, A1D5E2H1 and A1D11A7H10 (A), A1E7G5D1, A1E10G7H9, A2A1D2F1 and A2A5C7E8 (B), A2A6B1C2, A2G4C8G7 and A2H5F1A1 (C) to block human Siglec15-LRRC4C binding in a competitive ELISA.

Figure 6A:
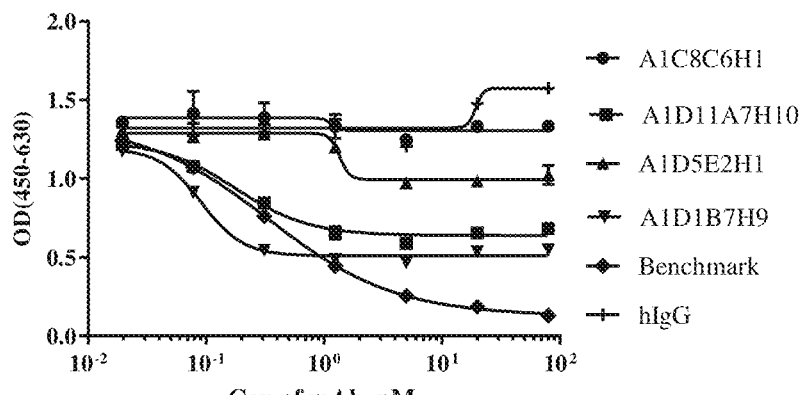
Figure 6B:
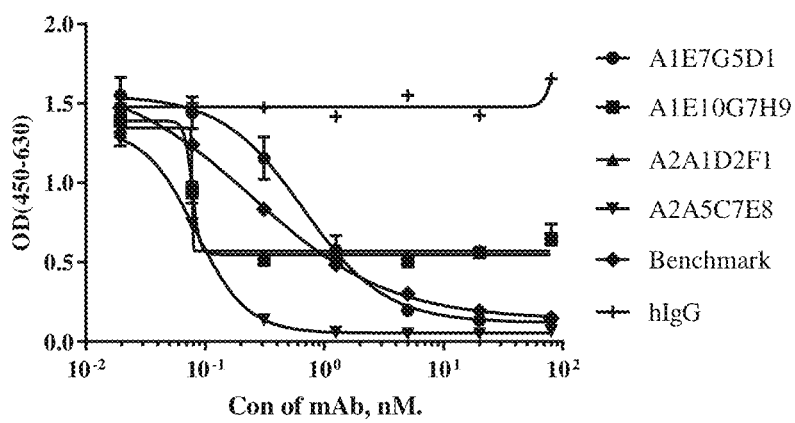
Figure 6C:
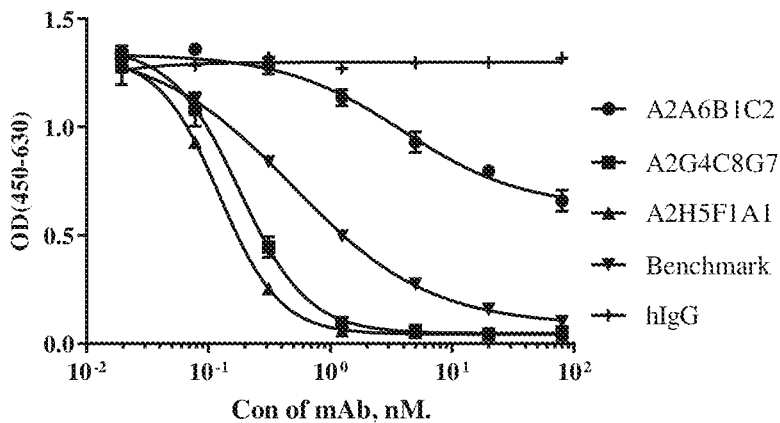

FIGS. 6A-6C show the abilities of antibodies A1C8C6H1, A1D1B7H9, A1D5E2H1 and A1D11A7H10 (A), A1E7G5D1, A1E10G7H9, A2A1D2F1 and A2A5C7E8 (B), A2A6B1C2, A2G4C8G7 and A2H5F1A1 (C) to block benchmark-human Siglec15 binding in a competitive ELISA.

Figure 7A:
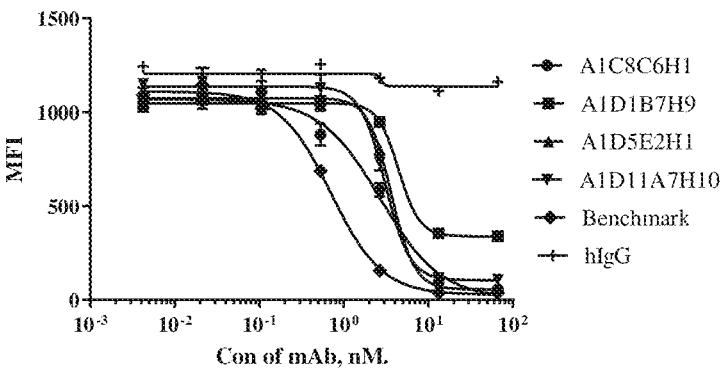
Figure 7B:
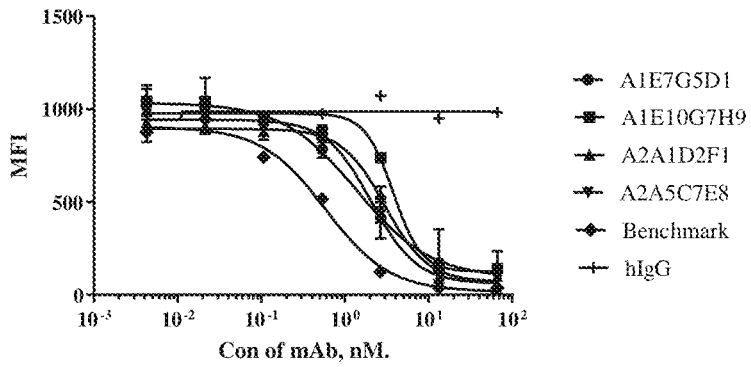
Figure 7C:
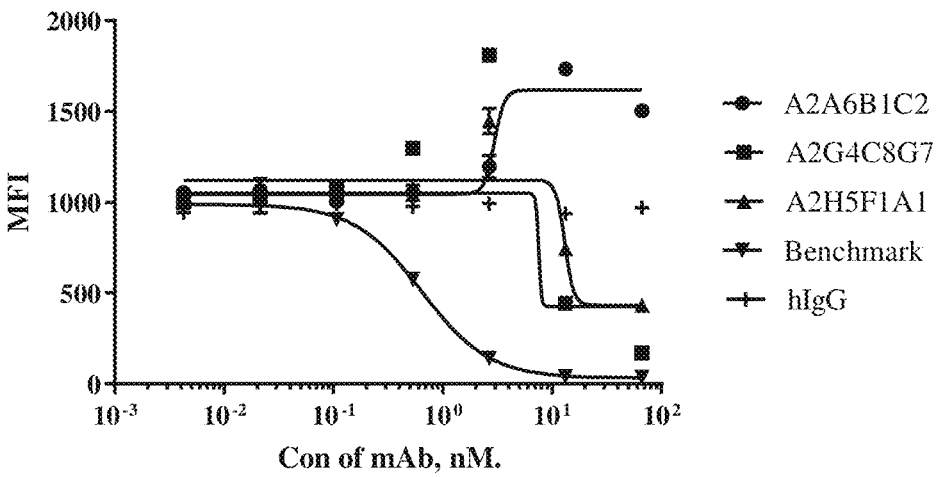

FIGS. 7A-7C show the abilities of antibodies A1C8C6H1, A1D1B7H9, A1D5E2H1 and A1D11A7H10 (A), A1E7G5D1, A1E10G7H9, A2A1D2F1 and A2A5C7E8 (B), A2A6B1C2, A2G4C8G7 and A2H5F1A1 (C) to block human Siglec15 to cell surface human LRRC4C in a cell based blocking FACS assay.

Figure 8A:
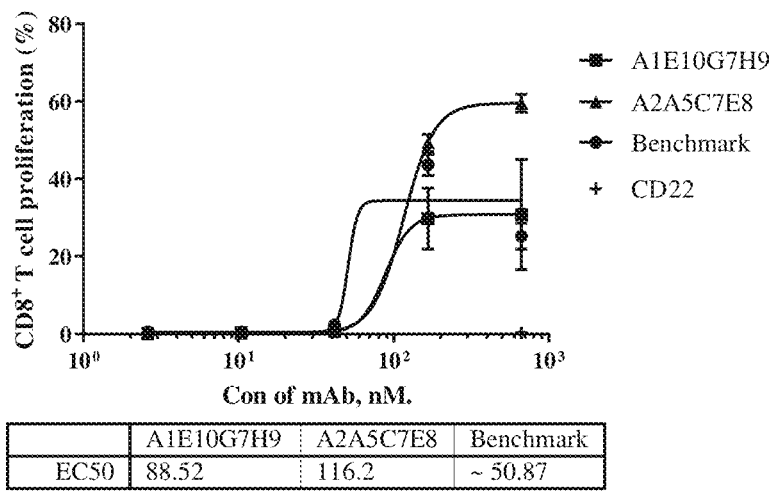
Figure 8B:
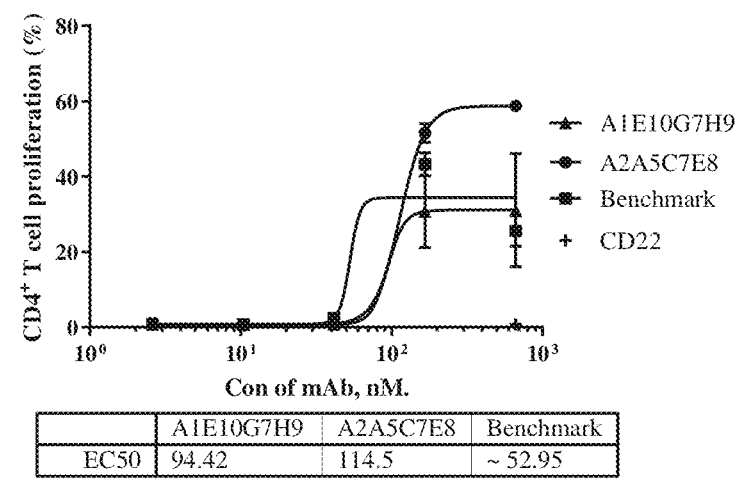

FIGS. 8A and 8B show that antibodies A2A5C7E8 and A1E10G7H9 reversed Siglec15 induced $CD8^+$ cell (A) and $CD4^+$ cell (B) suppression in a cell based functional assay.

Figure 9:
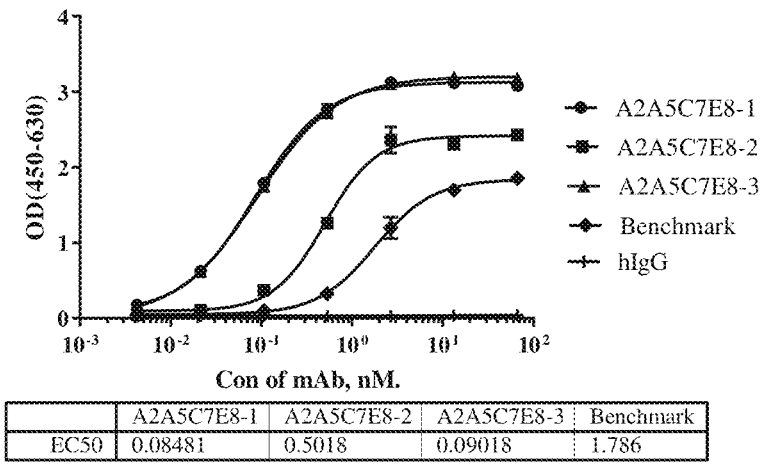

FIG. 9 shows the binding capacities of antibodies A2A5C7E8-1, A2A5C7E8-2 and A2A5C7E8-3 to human Siglec15 in a capture ELISA.

Figure 10:
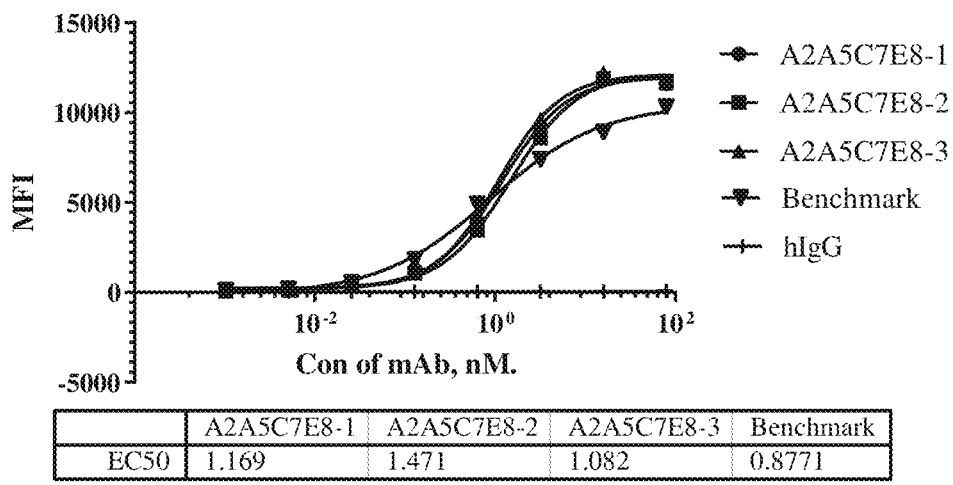

FIG. 10 shows the binding capacities of antibodies A2A5C7E8-1, A2A5C7E8-2 and A2A5C7E8-3 to human-siglec15-2D3-1E1 cells expressing human Siglec15 in a cell based binding FACS assay.

Figure 11:
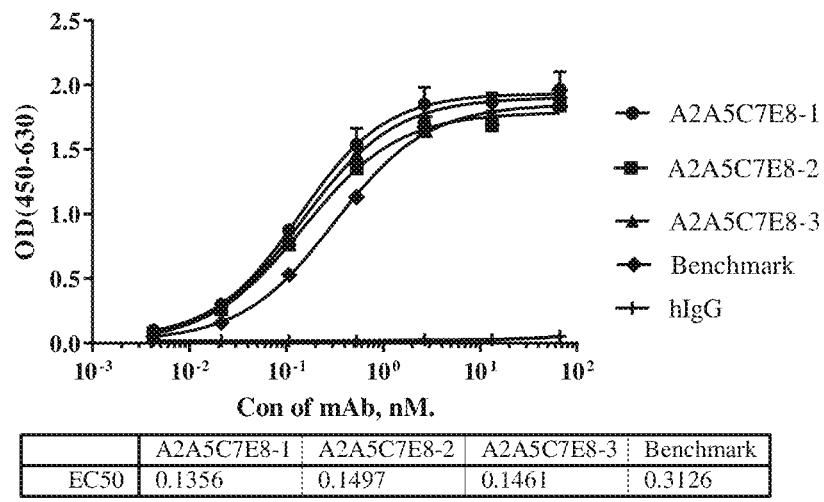

FIG. 11 shows the binding capacities of antibodies A2A5C7E8-1, A2A5C7E8-2 and A2A5C7E8-3 to cynomolgus Siglec15 in an indirect ELISA.

Figure 12:
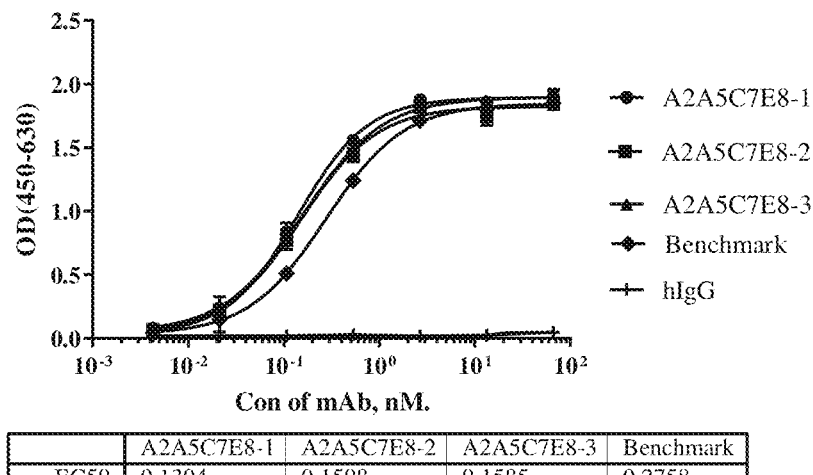

FIG. 12 shows the binding capacities of antibodies A2A5C7E8-1, A2A5C7E8-2 and A2A5C7E8-3 to mouse Siglec15 in an indirect ELISA.

Figure 13:
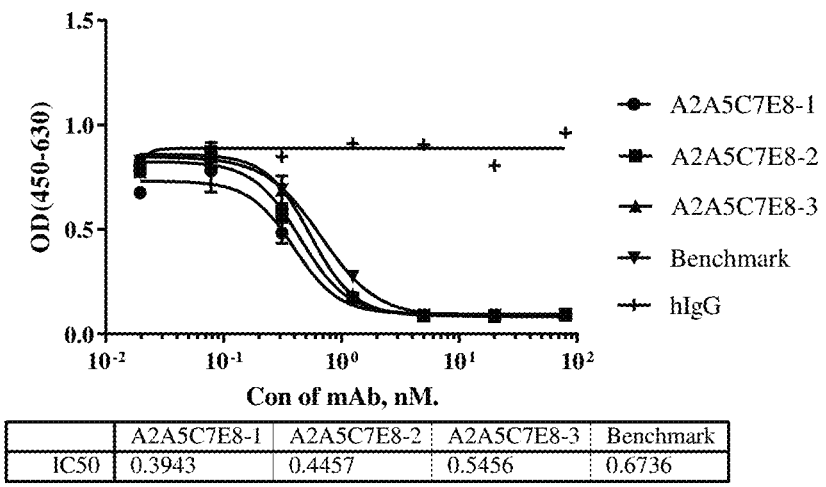

FIG. 13 shows the abilities of antibodies A2A5C7E8-1, A2A5C7E8-2 and A2A5C7E8-3 to block human Siglec15-LRRC4C binding in a competitive ELISA.

Figure 14:
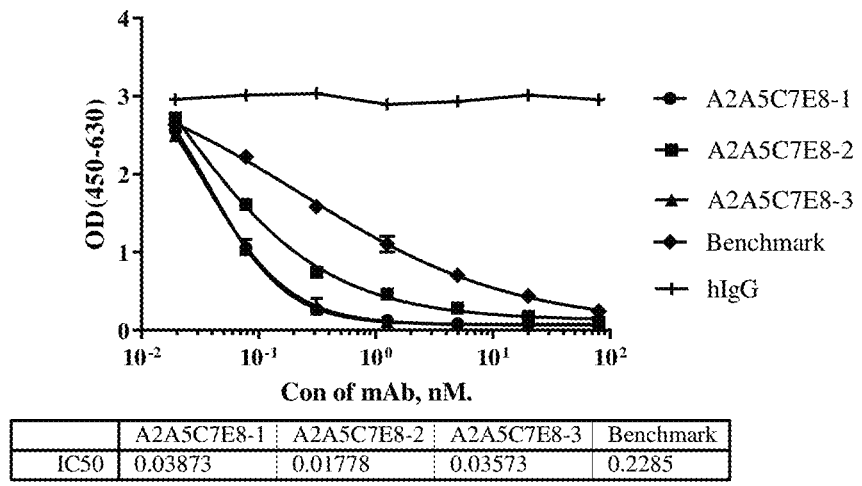
Figure 15A:
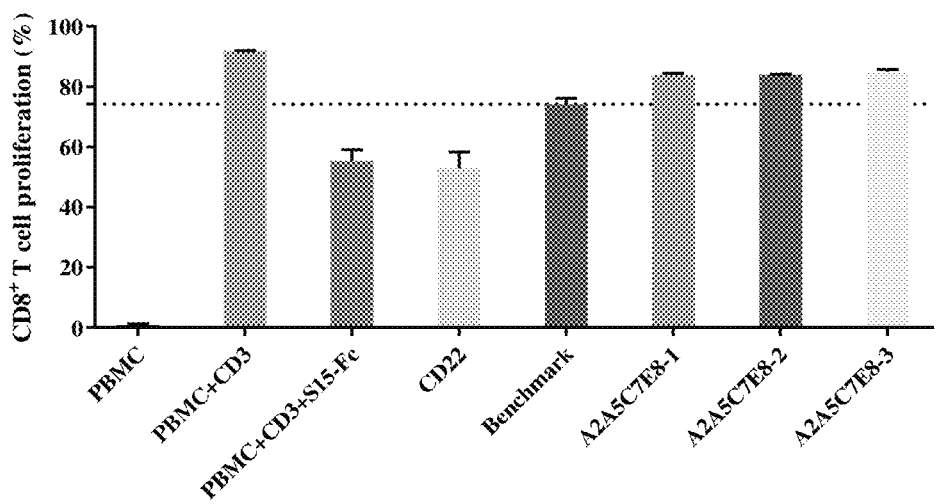
Figure 15B:
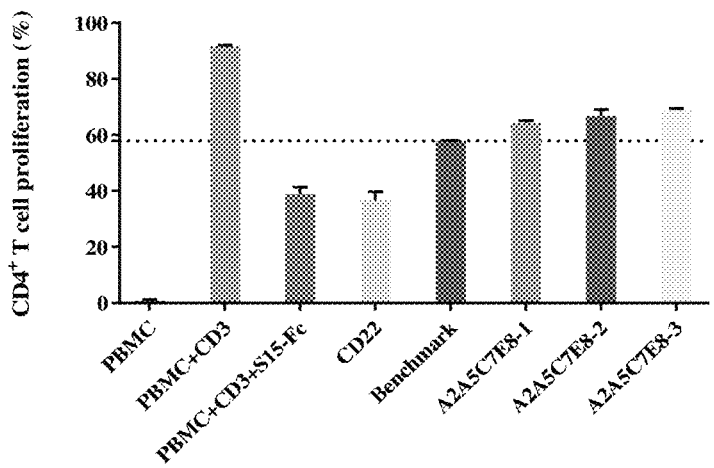
Figure 15C:
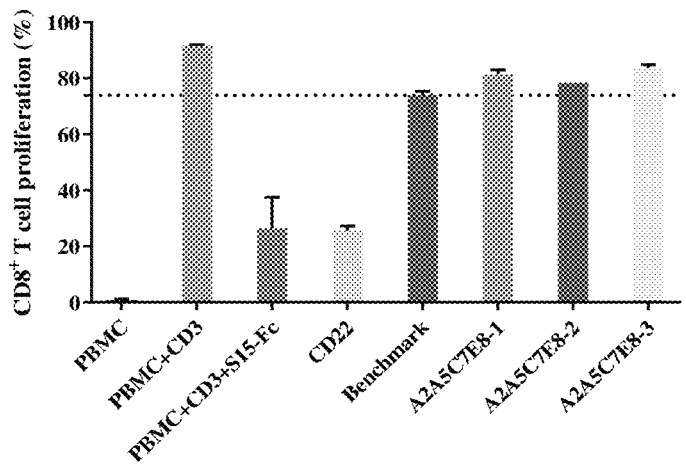
Figure 15D:
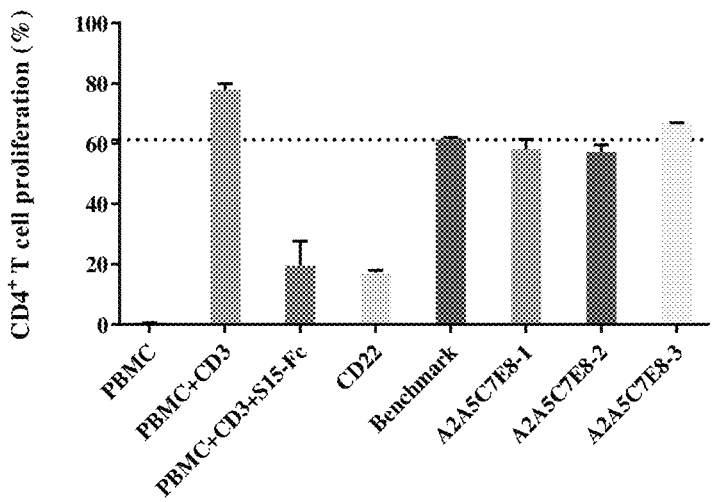

FIG. 14 shows the abilities of antibodies A2A5C7E8-1, A2A5C7E8-2 and A2A5C7E8-3 to block benchmark-human Siglec15 binding in a competitive ELISA.

FIGS. 15A-15D show that antibodies A2A5C7E8-1, A2A5C7E8-2 and A2A5C7E8-3 reversed $CD8^+$ cell (A) and $CD4^+$ cell (B) suppression induced by 93.5 nM Siglec15, and $CD8^+$ cell (C) and $CD4^+$ cell (D) suppression induced by 186.9 nM Siglec15 in a cell based functional assay.

Figure 16:
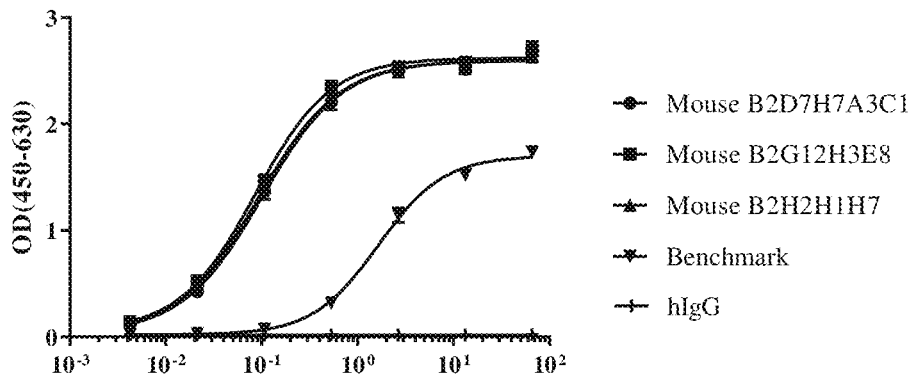

FIG. 16 shows the binding capacities of mouse antibodies B2D7H7A3C1, B2G12H3E8 and B2H2H1H7 to human Siglec15 in a capture ELISA.

Figure 17:
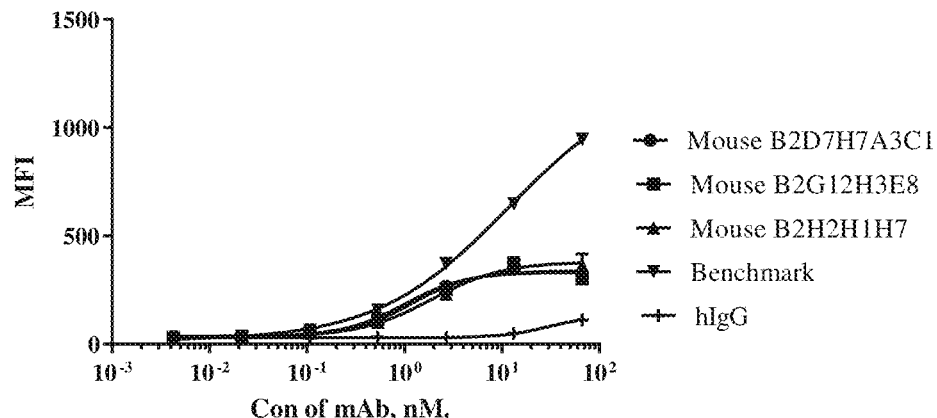

FIG. 17 shows the binding capacities of mouse antibodies B2D7H7A3C1, B2G12H3E8 and B2H2H1H7 to human-siglec15-2D3-1E1 cells expressing human Siglec15 in a cell based binding FACS assay.

Figure 18:
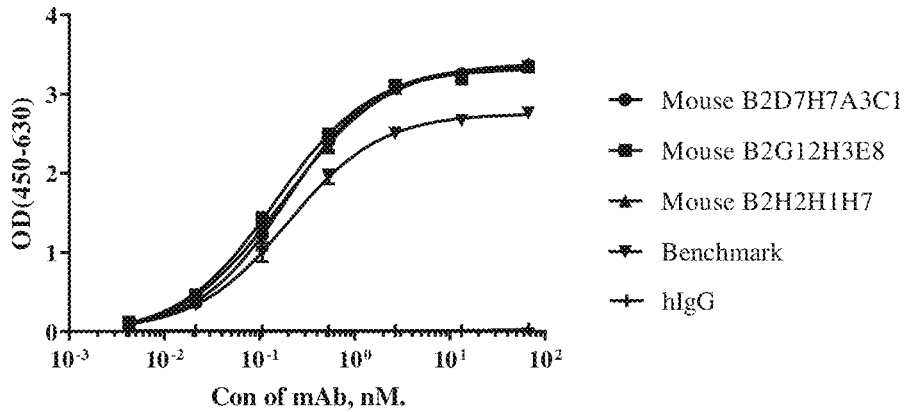

FIG. 18 shows the binding capacities of mouse antibodies B2D7H7A3C1, B2G12H3E8 and B2H2H1H7 to cynomolgus Siglec15 in an indirect ELISA.

Figure 19:
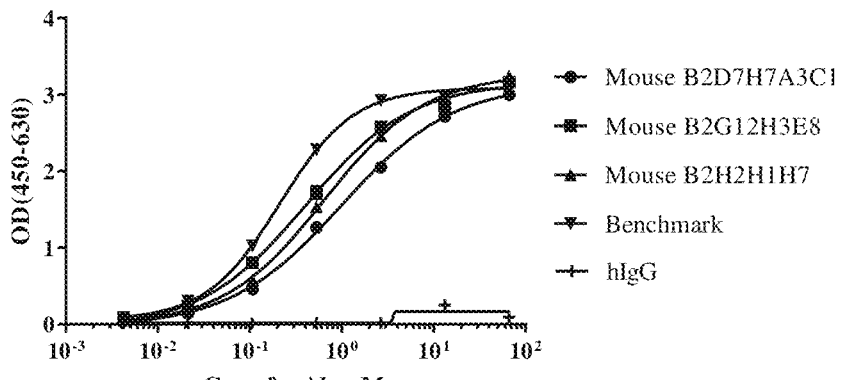

FIG. 19 shows the binding capacities of mouse antibodies B2D7H7A3C1, B2G12H3E8 and B2H2H1H7 to mouse Siglec15 in an indirect ELISA.

Figure 20:
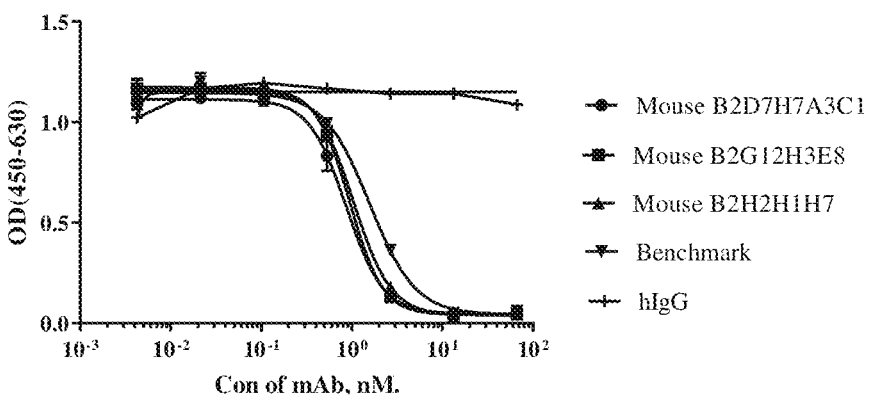

FIG. 20 shows the abilities of mouse antibodies B2D7H7A3C1, B2G12H3E8 and B2H2H1H7 to block human Siglec15-LRRC4C binding in a competitive ELISA.

Figure 21:
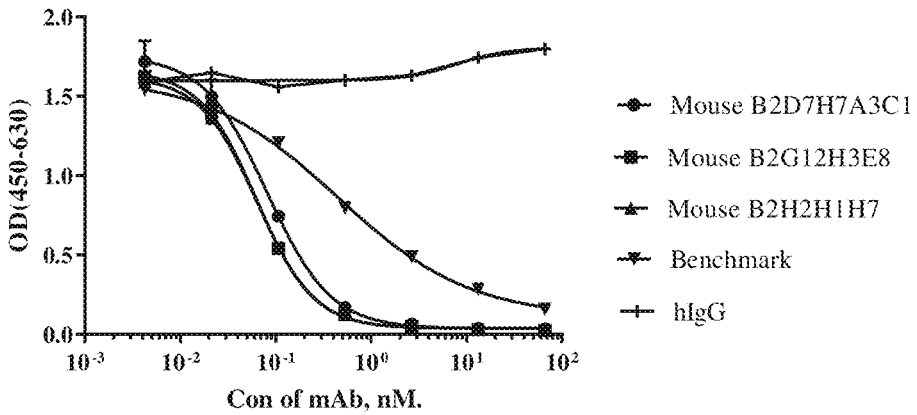

FIG. 21 shows the abilities of mouse antibodies B2D7H7A3C1, B2G12H3E8 and B2H2H1H7 to block benchmark-human Siglec15 binding in a competitive ELISA.

Figure 22A:
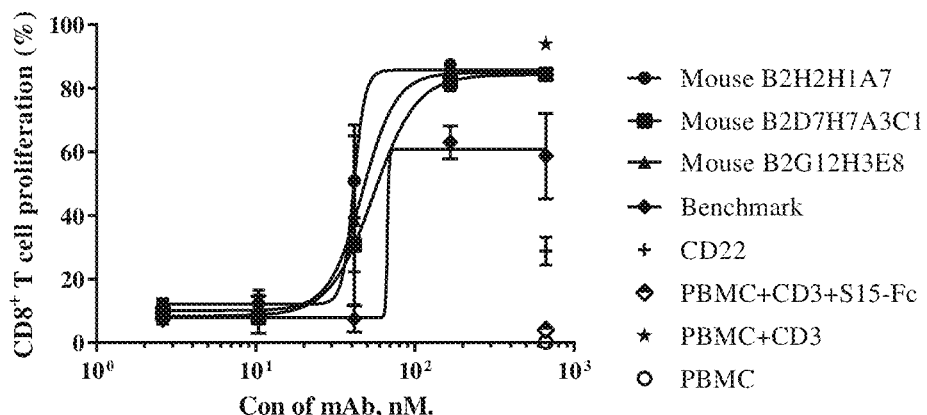
Figure 22B:
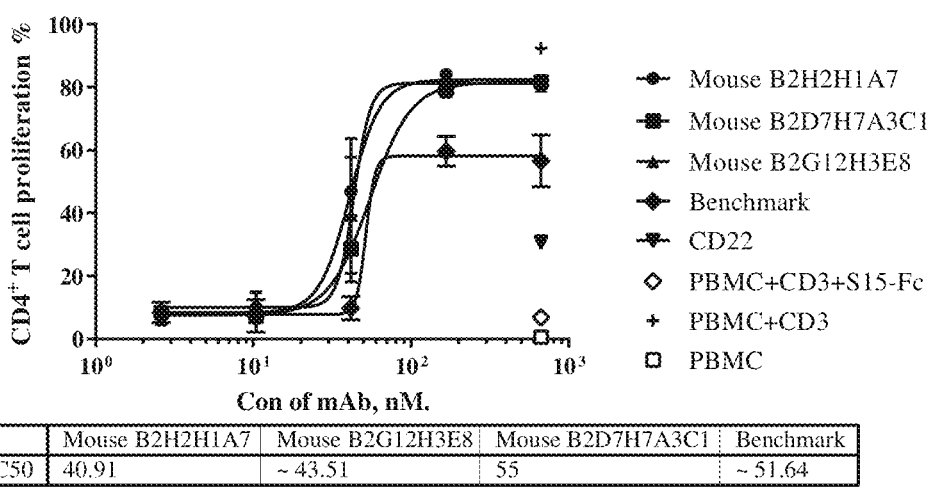

FIGS. 22A and 22B show that mouse antibodies B2D7H7A3C1, B2G12H3E8 and B2H2H1H7 reversed Siglec15 mediated $CD8^+$ cell (A) and $CD4^+$ cell (B) suppression in a cell based functional assay.

DETAILED DESCRIPTION OF THE INVENTION

To ensure that the present disclosure may be more readily understood, certain terms are first defined. Additional definitions are set forth throughout the detailed description.

The term "Siglec15" comprises variants, isoforms, homologs, orthologs and paralogs. For example, an antibody specific for a human Siglec15 protein may, in certain cases, cross-react with a Siglec15 protein from a species other than human, such as monkey. In other embodiments, an antibody specific for a human Siglec15 protein may be completely specific for the human Siglec15 protein and exhibit no cross-reactivity to other species or of other types, or may cross-react with Siglec15 from certain other species but not all other species.

The term "human Siglec15" refers to a Siglec15 protein having an amino acid sequence from a human, such as the amino acid sequence of human Siglec15 having a GenBank® accession number of Q6ZMC9. The terms "monkey or rhesus Siglec15" and "mouse Siglec15" refer to monkey and mouse Siglec15 sequences, respectively, e.g. those with the amino acid sequences having GenBank® Accession Nos. XP_028694069.1 and NP_001094508.1, respectively.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term "antibody" as used herein refers to an immunoglobulin molecule that recognizes and specifically binds a target, such as Siglec 15, through at least one antigen-binding site wherein the antigen-binding site is usually within the variable region of the immunoglobulin molecule. As used herein, the term encompasses intact polyclonal antibodies, intact monoclonal antibodies, single-chain Fv (scFv) antibodies, heavy chain antibodies (HCAbs), light chain antibodies (LCAbs), multispecific antibodies, bispecific antibodies, monospecific antibodies, monovalent antibodies, fusion proteins comprising an antigen-binding site of an antibody, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes. Unless expressly indicated otherwise, the term "antibody" as used herein include "antigen-binding portion" of the intact antibodies. An IgG is a glycoprotein which may comprise two heavy (H) chains and two light (L) chains inter-connected by disulfide bonds. Each heavy chain may be comprised of a heavy chain variable region (abbreviated herein as $V_H$) and a heavy chain constant region. The heavy chain constant region may be comprised of three domains, $C_{H1}$, $C_{H2}$ and $C_{H3}$. Each light chain may be comprised of a light chain variable region (abbreviated herein as $V_L$) and a light chain constant region. The light chain constant region may be comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a Siglec 15 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a Siglec15 protein is substantially free of antibodies that specifically bind antigens other than Siglec15 proteins). An isolated antibody that specifically binds a human Siglec15 protein may, however, have cross-reactivity to other antigens, such as Siglec15 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species have been grafted onto human framework sequences.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human Siglec15" is intended to refer to an antibody that binds to human Siglec15 protein (and possibly a Siglec15 protein from one or more non-human species) but does not substantially bind to non-Siglec15 proteins. Preferably, the antibody binds to human Siglec15 protein with "high affinity", namely with a $K_D$ of $5.0 \times 10^{-9}$ M or less, more preferably $1.0 \times 10^{-9}$ M or less, and more preferably $1.0 \times 10^{-10}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $5.0 \times 10^{-9}$ M or less, more preferably $1.0 \times 10^{-9}$ M or less, even more preferably $5.0 \times 10^{-10}$ M or less, even more preferably $1.0 \times 10^{-10}$ M or less and even more preferably $5.0 \times 10^{-11}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a BiaCore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody or antigen-binding portion thereof of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

The antibody, or the antigen-binding portion thereof, of the disclosure specifically binds to human or monkey Siglec15 with comparable, if not better, binding affinity as compared to previously described anti-Siglec15 antibodies, such as Siglec15-ch5G9.

Additional functional properties include the capacity to block Siglec15 binding to its ligand, and to reverse Siglec15 mediated T cell suppression.

The exemplary antibody or antigen-binding portion thereof of the disclosure is structurally and chemically characterized as described below and in the Examples. The amino acid sequence ID numbers of the heavy/light chain variable regions of the antibodies are summarized in Table 1 below. The heavy chain constant region for the antibodies may be human IgG1 heavy chain constant region having an amino acid sequence set forth in, e.g., SEQ ID NO: 17, and the light chain constant region for the antibodies may be human kappa constant region having an amino acid sequence set forth in, e.g., SEQ ID NO: 18. The antibody of the disclosure may be human, mouse, chimeric or humanized antibody.

The heavy chain variable region CDRs and the light chain variable region CDRs in Table 1 have been defined by the Kabat numbering system. However, as is well known in the art, CDR regions can also be determined by other systems such as Chothia, and IMGT, AbM or Contact numbering system/method, based on heavy chain/light chain variable region sequences.

TABLE 1

Amino acid sequence ID numbers of heavy/light chain variable regions

| Antibody | $V_H$ CDR1 | $V_H$ CDR2 | $V_H$ CDR3 | $V_H$ | $V_L$ CDR1 | $V_L$ CDR2 | $V_L$ CDR3 | $V_L$ |
|---|---|---|---|---|---|---|---|---|
| A2A5C7E8 | 1 | 44 | 3 | 47 | 4 | 5 | 6 | 8 |
| A2A5C7E8-2 | 1 | 45 | 3 | 48 | 4 | 5 | 6 | 8 |
| A2A5C7E8-3 | 1 | 46 | 3 | 49 | 4 | 5 | 6 | 8 |
| A1E10G7H9 | 9 | 10 | 11 | 15 | 12 | 13 | 14 | 16 |
| B2D7H7A3C1 | 33 | 34 | 35 | 39 | 36 | 37 | 38 | 42 |
| B2G12H3E8 | 33 | 34 | 35 | 40 | 36 | 37 | 38 | 42 |
| B2H2H1H7 | 33 | 34 | 35 | 41 | 36 | 37 | 38 | 43 |

The $V_H$ and $V_L$ sequences (or CDR sequences) of other anti-Siglec15 antibodies which bind to human Siglec15 can be "mixed and matched" with the $V_H$ and $V_L$ sequences (or CDR sequences) of the anti-Siglec15 antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another anti-Siglec15 antibody, wherein the antibody specifically binds human Siglec15.

In another embodiment, an antibody of the disclosure, or an antigen binding portion thereof, comprises:
(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-Siglec15 antibody, wherein the antibody specifically binds human Siglec15.

In yet another embodiment, the antibody, or antigen binding portion thereof, includes the heavy chain variable CDR2 region of anti-Siglec15 antibody combined with CDRs of other antibodies which bind human Siglec15, e.g., CDR1 and/or CDR3 from the heavy chain variable region, and/or CDR1, CDR2, and/or CDR3 from the light chain variable region of a different anti-Siglec15 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal 8: Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152:5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-Siglec15 antibody and at least the CDR3 of the heavy and/or light chain variable region of the anti-Siglec15 antibody, or the CDR3 of the heavy and/or light chain variable region of another anti-Siglec15 antibody, wherein the antibody is capable of specifically binding to human Siglec15. These antibodies preferably (a) compete for binding with Siglec15; (b) retain the functional characteristics; (c) bind to the same epitope; and/or (d) have a similar binding affinity as the anti-Siglec15 antibody of the present disclosure. In yet another embodiment, the antibodies further may comprise the CDR2 of the light chain variable region of the anti-Siglec15 antibody, or the CDR2 of the light chain variable region of another anti-Siglec15 antibody, wherein the antibody is capable of specifically binding to human Siglec15. In another embodiment, the antibodies of the disclosure may include the CDR1 of the heavy and/or light chain variable region of the anti-Siglec15 antibody, or the CDR1 of the heavy and/or light chain variable region of another anti-Siglec15 antibody, wherein the antibody is capable of specifically binding to human Siglec15.

In another embodiment, an antibody of the disclosure comprises a heavy and/or light chain variable region sequences of CDR1, CDR2 and CDR3 sequences which differ from those of the anti-Siglec15 antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and/or conservative modifications thereof; and/or (c) the heavy chain variable region CDR3 sequence comprises a sequence listed in Table 1 above, and/or conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human Siglec15.

The antibody or antigen-binding portion thereof of the present disclosure possesses one or more of the following functional properties described above, such as high affinity binding to human Siglec15, and the ability to reverse Siglec 15 mediated T cell suppression.

In various embodiments, the antibody or antigen-binding portion thereof can be, for example, a human, mouse, humanized or chimeric one.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-Siglec15 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the GenBank® database. For example, the following heavy chain germline sequences found in the HCo7 HuMAb Mouse® are available in the accompanying GenBank® Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb Mouse® are available in the accompanying GenBank® Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-Siglec15 monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "back mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (α (1, 6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. provisional patent application 60/836,998. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EPO 154 316 and EP 0 401 384.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-Siglec15 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-Siglec15 antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the Siglec15 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)$_3$ (SEQ ID NO:50), such that the $V_H$ and $V_L$ sequences can be expressed as a contiguous single-chain protein, with the $V_L$ and $V_H$ regions joined by the flexible linker (see e.g., Bird et al., (1988) Science 242:423-426; Huston et al., (1988) Proc. Natl. Acad. Sci. USA 85:5879-5883; McCafferty et al., (1990) Nature 348:552-554).

Monoclonal antibodies (mAbs) of the present disclosure may be produced using a transgenic mouse platform (e.g., CAMouse$^{HG}$, B000.60.01T(G15), HG5042, Chongqing Camab Biotech Ltd.), by immunizing transgenic mice genetically engineered to produce fully human antibodies with a target antigen, i.e., Siglec15 especially human Siglec15. Spleen cells from the immunized transgenic mice may be fused with myeloma cells according to the method as described in Kohler G, and Milstein C, "Continuous cultures of fused cells secreting antibody of predefined specificity," Nature, 256: 495-497 (1975). Fused "hybrid cells" are subsequently dispensed into plates, and surviving hybridoma colonies are observed under the microscope seven to ten days post fusion. After e.g., two weeks, the supernatant from each well can be subjected to antigen binding test, and positive hybridoma secreting desired antibodies are subcloned by limiting dilution to ensure the clonality of the cell line, and then monoclonal antibodies were purified.

The antibodies of the disclosure can also be prepared by other methods well known in the art, such as viral or oncogenic transformation of B lymphocytes and phage display techniques.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies of the disclosure can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059, 404; WO 08/083,312; and WO 08/103,693; U.S. Patent Publications 20060024317; 20060004081; and 20060247295; the disclosures of which are incorporated herein by reference.

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Also provided herein is an oncolytic virus that preferentially infects and kills cancer cells. Antibodies of the present disclosure can be used in conjunction with oncolytic viruses. Alternatively, oncolytic viruses encoding antibodies of the present disclosure can be introduced into human body.

Also provided herein are a chimeric antigen receptor (CAR) containing an anti-Siglec15 scFv, the anti-Siglec15 scFv comprising CDRs and heavy/light chain variable regions described herein.

The anti-Siglec15 CAR may comprise (a) an extracellular antigen binding domain comprising an anti-Siglec15 scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, comprising the CAR provided herein. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

In another aspect, the present disclosure provides a pharmaceutical composition which may comprise one or more antibodies or antigen-binding portions thereof, the bispecifics, CAR-T cells, oncolytic viruses, immunoconjugates, nucleic acid molecules, expression vectors, or host cells of the present disclosure formulated together with a pharmaceutically acceptable carrier. The antibodies or antigen-binding portion thereof, the bispecifics, CAR-T cells, oncolytic viruses, immunoconjugates, nucleic acid molecules, expression vectors, or host cells can be dosed separately when the composition contains more than one antibody (or antigen-binding portion thereof, the bispecifics, CAR-T cells, oncolytic viruses, immunoconjugates, nucleic acid molecules, expression vectors, or host cells). The composition may optionally contain one or more additional pharmaceutically active ingredients, such as another antibody or a drug, such as an anti-tumor drug.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg.

A "therapeutically effective dosage" of an anti-Siglec15 antibody, or the antigen-binding portion thereof, or the bispecifics, CAR-T cells, oncolytic viruses, immunoconjugates of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29: 685; Umezawa et al., (1988) *Biochem. Biophys. Res. Commun.* 153:1038; Bloeman et al., (1995)

FEBS Lett. 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) Immunomethods 4:273.

The compositions of the present disclosure have numerous in vitro and in vivo utilities involving, for example, treatment of cancers and osteoporosis. The antibodies can be administered to human subjects, e.g., in vivo, to inhibit tumor growth, or to inhibit bone loss.

Given the ability of anti-Siglec15 antibodies or antigen-binding portions of the disclosure to reverse Siglec15 mediated T cell suppression and inhibit proliferation and survival of cancer cells, the disclosure provides methods for inhibiting growth of tumor cells in a subject comprising administering to the subject the composition of the disclosure such that growth of the tumor is inhibited in the subject. Non-limiting examples of tumors that can be treated by the composition of the disclosure include, but not limited to, non-small cell lung cancer, ovarian cancer, melanoma, colorectal cancer, breast cancer (including triple-negative breast cancer), head and neck squamous cell carcinoma, endometrial cancer, and squamous cell carcinoma. Additionally, refractory or recurrent malignancies whose growth may be inhibited using the antibodies of the disclosure.

In another aspect, the disclosure provides a method for inhibiting bone loss or increasing bone mass, comprising administering to the subject a therapeutically effective amount of the antibody, or antigen-binding portion thereof, of the disclosure.

In another aspect, the disclosure provides methods of combination therapy in which the anti-Siglec15 antibodies, or antigen-binding portion thereof, or the bispecifics, CAR-T cells, oncolytic viruses, immunoconjugates of the present disclosure are co-administered with one or more additional antibodies that are effective in inhibiting tumor growth in a subject. In one embodiment, the disclosure provides a method for inhibiting tumor growth in a subject comprising administering to the subject an anti-Siglec15 antibody (or antigen-binding portion thereof, or the CAR-T cell, oncolytic virus, immunoconjugate) and one or more additional antibodies, such as an anti-VISTA antibody, an anti-LAG-3 antibody, an anti-PD-L1 antibody, and anti-PD-1 antibody and/or an anti-CTLA-4 antibody. In certain embodiments, the subject is human.

The Siglec15 signaling activation can also be further combined with standard cancer treatments. For example, Siglec15 signaling blockade can be combined with CTLA-4 and/or LAG-3 and/or PD-1 blockade and also chemotherapeutic regimes. For example, a chemotherapeutic agent can be administered with the anti-Siglec15 antibodies, which may be a cytotoxic agent. For example, epirubicin, oxaliplatin, and 5-FU are administered to patients receiving anti-Siglec15 therapy.

Optionally, the combination of anti-Siglec15 and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) 1 Immunol. 173:4919-28). Non-limiting examples of tumor vaccines that can be used include peptides of melanoma antigens, such as peptides of gp100, MAGE antigens, Trp-2, MART 1 and/or tyrosinase, or tumor cells transfected to express the cytokine GM-CSF.

Other therapies that may be combined with anti-Siglec15 therapy includes, but not limited to, interleukin-2 (IL-2) administration, radiation, surgery, or hormone deprivation.

In another aspect, the disclosure provides methods of combination therapy in which the anti-Siglec15 antibodies, or antigen-binding portion thereof, or the bispecifics, CAR-T cells, oncolytic viruses, immunoconjugates of the present disclosure are co-administered with one or more additional agents effective in inhibiting bone loss. In one embodiment, the disclosure provides a method for inhibiting bone loss in a subject comprising administering to the subject an anti-Siglec15 antibody (or antigen-binding portion thereof, or the CAR-T cell, oncolytic virus, immunoconjugates) and one or more additional antibodies for osteoporosis treatment, such as an anti-RANKL antibody, and an anti-IL-11 antibody. In certain embodiments, the subject is human.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, GenBank® sequences, patents and published patent applications cited throughout this application are expressly incorporated herein by reference.

EXAMPLES

Example 1 Generation of Human Anti-Siglec15 Monoclonal Antibodies Using Hybridoma Technology Immunization A transgenic mouse platform CAMouse$^{HG}$ (HG5042, Chongqing CAMAB Biotech Ltd.) was used to produce fully human antibodies. The transgenic mice were immunized according to the method as described in E Harlow, D. Lane, Antibody: A Laboratory Manual, Cold Spring Harbor Laboratory Press, Cold Spring Harbor, N.Y., 1998. In house made recombinant human Siglec15 protein with human IgG1 Fc at the C-terminus (amino acid sequence set forth in SEQ ID NO: 19) was used as the immunogen, and in house made cynomolgus monkey Siglec15-his protein (amino acid sequence set forth in SEQ ID NO: 21) was used for determining anti-sera titer and for screening hybridomas secreting antigen-specific antibodies. Immunizing dosages contained 50 μg human Siglec15-Fc protein/mouse/injection for both primary and boost immunizations. To increase immune response, the complete Freund's adjuvant and incomplete Freund's adjuvant (Sigma, St. Louis, Mo., USA) were used respectively for primary and boost immunizations. Briefly, adjuvant-antigen mixture was prepared by first gently mixing the adjuvant in a vial using a vortex. The desired amount of adjuvant was transferred to an autoclaved 1.5 mL micro-centrifuge tube. The antigen was prepared in PBS or saline with concentration ranging from 0.5-0.67 mg/ml. The calculated amount of antigen was then added to the micro-centrifuge tube with the adjuvant, and the resulting mixture was mixed by gently vortexing for 2 minutes to generate water-in-oil emulsions. The adjuvant-antigen emulsion was then drawn into the proper syringe for animal injection. A total of 50 µg antigen was injected in a volume of 150-200 µl. Each animal was immunized, and then boosted for 3 to 4 times depending on the anti-sera titer. Animals with good titers were given a final boost by intraperitoneal injection before fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," Nature, 256: 495-497 (1975). Fused "hybrid cells" were subsequently dispensed into 96-well plates in DMEM/20% FCS/HAT medium. Surviving hybridoma colonies were observed under the microscope seven to ten days post fusion. After two weeks, the supernatant from each well was subject to indirect ELISA using recombinant cynomolgus monkey Siglec15-his protein. Positive hybridomas secreting antibodies that bound to cynomolgus Siglec15-his protein were then selected and transferred to 24-well plates. These hybridoma clones were further tested for their activities of blocking human Siglec 15-LRRC4C binding. Hybridoma clones producing antibodies that showed high specific cynomolgus Siglec15 binding and Siglec15-LRRC4C blocking activities were subcloned by limiting dilution to ensure the clonality of the cell line, and then monoclonal antibodies were purified. Briefly, Protein A Sepharose™ columns (from Bestchrom (Shanghai) Biosciences, Cat #AA0273) were washed using PBS buffer in 5 to 10 column volumes. Cell supernatants of hybridoma monoclones were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris©-HCl, pH 9.0). Fractions containing immunoglobulins were pooled and dialyzed in PBS overnight at 4° C. Subsequently, the in vitro functional activities of purified monoclonal antibodies were characterized as follows.

Example 2 Binding Affinity Determination of Anti-Siglec15 Monoclonal Antibodies Using BiaCore™ Surface Plasmon Resonance The purified anti-Siglec15 monoclonal antibodies (mAbs) generated in Example 1 were characterized for binding affinity and binding kinetics by BiaCore™ T200 system (GE HealthCare, Pittsburgh, Pa., USA).

Briefly, goat anti-human IgG (GE healthcare, Cat #BR100839, Human Antibody Capture Kit) was covalently linked to a CM5 chip (carboxy methyl dextran coated chip, GE HealthCare, Cat #BR-1005-30) via primary amines, using a standard amine coupling kit provided by BiaCore™ (GE HealthCare, Pittsburgh, Pa., USA). Un-reacted moieties on the biosensor surface were blocked with ethanolamine. Then, purified anti-Siglec15 antibodies of the disclosure at the concentration of 13.3 nM and an anti-Siglec15 benchmark (ch5G12, also referred to as BM, see U.S. Patent Publication No. 20190202912A1, amino acid sequences of the heavy chain and light chain set forth in SEQ ID NOs: 24 and 25, respectively) at 13.3 nM, were respectively flowed onto the chip at a flow rate of 10 µL/min. Then, serially diluted recombinant human Siglec15-his protein (in house made, amino acid sequence set forth in SEQ ID NO: 20) or cynomolgus monkey Siglec15-his protein (in house made, amino acid sequence set forth in SEQ ID NO: 21), 2-fold serial dilution in HBS-E13$^+$ buffer starting at 80 nM, were respectively flown onto the chip at a flow rate of 30 µL/min. The antigen-antibody association kinetics was followed for 2 minutes and the dissociation kinetics was followed for 10 minutes. The association and dissociation curves were fit to a 1:1 Langmuir binding model using BiaCore™ evaluation software. The $K_D$, $K_a$ and $K_d$ values were determined and summarized in Table 2 below.

TABLE 2

Binding affinity of anti-Siglec15 antibodies

| | Kinetics on Biacore | | | | | |
|---|---|---|---|---|---|---|
| | Human Siglec15-his | | | Cynomolgus Siglec15-his | | |
| Clone ID# | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| A1E7G5D1 | 2.94E+05 | 6.04E−05 | 2.05E−10 | 1.69E+05 | 9.22E−05 | 5.44E−10 |
| A1C8C6H1 | 2.93E+05 | 7.05E−04 | 2.41E−09 | 1.34E+05 | 4.23E−04 | 3.15E−09 |
| A1D11A7H10 | 2.18E+06 | 5.27E−04 | 2.42E−10 | 1.02E+06 | 3.40E−04 | 3.33E−10 |
| A2A1D2F1 | 3.29E+06 | 2.65E−04 | 8.04E−11 | 1.68E+06 | 2.19E−04 | 1.30E−10 |
| A2A6B1C2 | 3.07E+05 | 4.79E−04 | 1.56E−09 | 1.61E+05 | 3.60E−04 | 2.24E−09 |
| A1D5E2H1 | 2.74E+05 | 2.04E−04 | 7.45E−10 | 1.72E+05 | 2.20E−04 | 1.28E−09 |
| A2A5C7E8 | 2.43E+06 | 9.98E−05 | 4.10E−11 | 1.25E+06 | 8.49E−05 | 6.81E−11 |
| A2H5F1A1 | 1.57E+06 | 1.84E−04 | 1.17E−10 | 4.15E+05 | 2.76E−04 | 6.66E−10 |
| A1E10G7H9 | 7.18E+06 | 1.00E−04 | 1.39E−11 | 3.89E+06 | 1.04E−04 | 2.69E−11 |
| A2G4C8G7 | 1.27E+06 | 1.97E−04 | 1.54E−10 | 2.93E+05 | 2.96E−04 | 1.01E−09 |
| A1D1B7H9 | 1.73E+06 | 1.48E−04 | 8.56E−11 | 1.07E+06 | 1.22E−04 | 1.14E−10 |
| Benchmark | 6.51E+06 | 0.001722 | 2.65E−10 | 1.76E+06 | 7.88E−04 | 4.48E−10 |

All the anti-Siglec15 antibodies of the disclosure specifically bound to human Siglec15 and cynomolgus monkey Siglec15 with comparable or higher binding affinity compared to benchmark. The antibodies A2A1D2F1, A2A5C7E8, A1E10G7H9 and A1D1B7H9 showed the highest binding affinity.

Example 3 Siglec15 Binding Activity of Anti-Siglec15 Antibodies

The antibodies of the disclosure were further tested for the binding activity to Siglec15 by Capture ELISA, Flow Cytometry (FACS) and indirect ELISA.

3.1 Capture ELISA

Briefly, 96-well plates were coated with 100 μl of 2 μg/ml AffiniPure Goat Anti-Human IgG F(ab')$_2$ fragment specific (Jackson Immuno Research, Cat #109-005-097) in PBS for 2 hours at 37° C. Plates were washed once with wash buffer (PBS+0.05% v/v Tween®-20, PBST) and then blocked with 200 μl blocking buffer (5% w/v non-fatty milk in PBST) overnight at 4° C. Plates were washed 4 times and respectively incubated with 100 μl serially diluted anti-Siglec15 antibodies of the disclosure, the benchmark and hIgG (human immunoglobulin (pH4) for intravenous injection, Hualan Biological Engineering Inc.), 5-fold dilution in 2.5% w/v non-fatty milk in PBST starting at 66.7 nM, for 40 minutes at 37° C., and then washed 4 times again. Plates containing captured antibodies were incubated with 100 μl biotin-labeled human Siglec15-his protein (in house made with SEQ ID NO: 20, 145 ng/ml in 2.5% w/v non-fatty milk in PBST) for 40 minutes at 37° C., washed 4 times, and incubated with streptavidin conjugated HRP (1:10000 dilution in PBST, Jackson Immuno Research, Cat #016-030-084, 100 μl/well) for 40 minutes at 37° C. After a final wash, plates were incubated with 100 μl/well ELISA substrate TMB (Innoreagents, Cat #TMB-S-002). The reaction was stopped in 4 minutes at room temperature with 50 μl/well 1M H$_2$SO$_4$, and the absorbance of each well was read on a microplate reader using dual wavelength mode with 450 nm for TMB and 630 nm as the reference wavelength, then the OD (450-630) values were plotted against antibody concentration. Data was analyzed using GraphPad Prism software and EC$_{50}$ values were reported.

3.2 Cell Based Binding FACS

The binding activities of the anti-Siglec15 antibodies to cell surface Siglec15 were tested by flow cytometry (FACS), using in-house prepared human-siglec15-2D3-1E1 cells expressing human Siglec15 (amino acid residues Met1-Pro328 of uniprot #Q6ZMC9) on cell membranes. The human-siglec15-2D3-1E1 cells were prepared by transfecting HEK-293 cells (ATCC®#CRL-1573) with pCMV-T-P plasmids inserted with human Siglec15 coding sequence between EcoRI and XbaI sites, following the instruction of Lipofectamine™ 3000 transfection reagent (Thermo Fisher). The human-siglec15-2D3-1E1 cells were harvested from cell culture flasks, washed twice and re-suspended in phosphate buffered saline (PBS) containing 2% v/v Fetal Bovine Serum (FACS buffer). 2×10$^5$ cells per well in 96 well-plates were incubated in 100 μL serially diluted anti-Siglec15 antibodies or controls (starting at 66.67 nM, 5-fold serial dilution) in FACS buffer for 40 minutes on ice. Cells were washed twice with FACS buffer, and 100 μL R-Phycoerythrin AffiniPure Goat Anti-Human IgG, Fcγ Fragment Specific (1:1000 dilution in FACS buffer, Jackson Immunoresearch, Cat #109-115-098) was added. Following a 40-minute incubation at 4° C. in dark, cells were washed three times and re-suspended in FACS buffer. Fluorescence was measured using a Becton Dickinson FACSCanto II™-HTS equipment. Data was analyzed using GraphPad Prism software and EC$_{50}$ values were reported.

3.3 Indirect ELISA

The anti-Siglec15 antibodies' cross-reactions to cynomolgus or mouse Siglec15 proteins were measured. Briefly, 96-well micro plates were coated with 100 μl of 2 μg/ml cynomolgus Siglec15-his protein (in house made with SEQ ID NO: 21), or 2 μg/ml mouse Siglec15-his protein (in house made with SEQ ID NO: 22) in carbonate/bicarbonate buffer (pH 9.6) for 2 hours at 37° C. ELISA plates were washed once with wash buffer (PBS+0.05% v/v Tween®-20, PBST) and then blocked with 200 μl/well blocking buffer (5% w/v non-fatty milk in PBST) overnight at 4° C. Plates were washed 4 times and incubated with 100 μl serially diluted anti-Siglec15 antibodies of the disclosure or controls (starting at 66.7 nM, 5-fold serial dilution in PBST with 2.5% w/v non-fatty milk) for 40 minutes at 37° C. ELISA plates were washed 4 times again and incubated with Peroxidase AffiniPure Goat Anti-Human IgG, F(ab)$_2$ fragment specific (1:5000 dilution in PBST buffer, Jackson Immunoresearch, Cat #109-035-097, 100 μl/well) for 40 minutes at 37° C. After a final wash, plates were incubated with 100 μl/well TMB (Innoreagents, Cat #TMB-S-002). The reaction was stopped 4 minutes later at room temperature with 50 μl 1M H$_2$SO$_4$, and the absorbance of each well was read on a microplate reader using dual wavelength mode with 450 nm for TMB and 630 nm as the reference wavelength, then the OD (450-630) values were plotted against antibody concentration. Data was analyzed using GraphPad Prism software and EC$_{50}$ values were reported.

The results of the three assays were shown in FIGS. 1A-1C to 4A-4C.

Figure 1A:
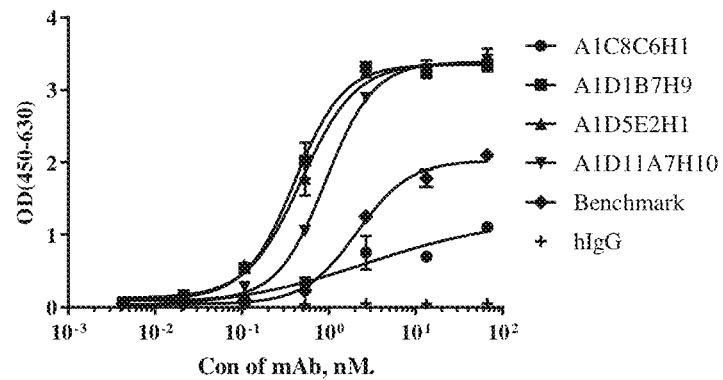
FIGS. 1A-1C show the binding capacities of antibodies A1C8C6H1, A1D1B7H9, A1D5E2H1 and A1D11A7H10 (A), A1E7G5D1, A1E10G7H9, A2A1D2F1 and A2A5C7E8 (B), A2A6B1C2, A2G4C8G7 and A2H5F1A1 (C) to human Siglec15 in a capture ELISA.
Figure 1B:
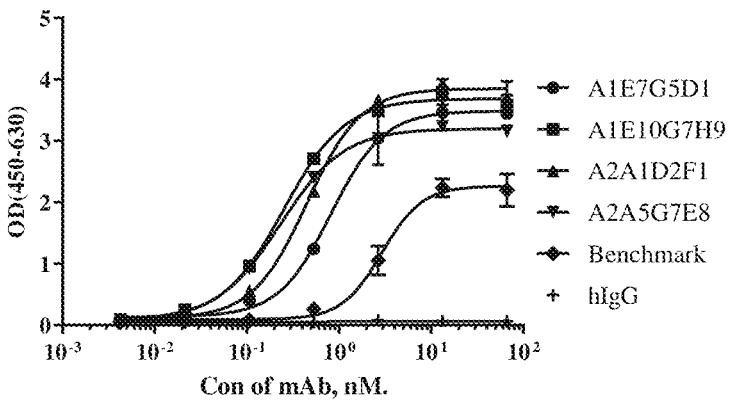
Figure 1C:
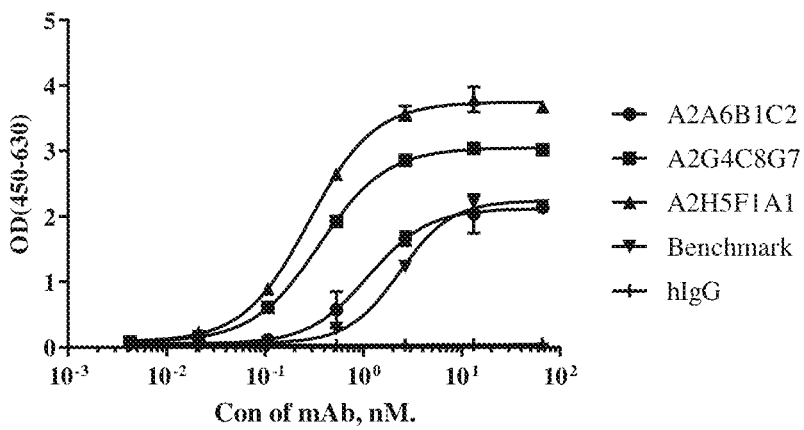

It can be seen from FIGS. 1A-1C that all antibodies of the disclosure, except A1C8C6H1, specifically bound to the human Siglec15, with lower EC$_{50}$ and higher Bmax (maximum binding) than the benchmark.

Figure 2A:
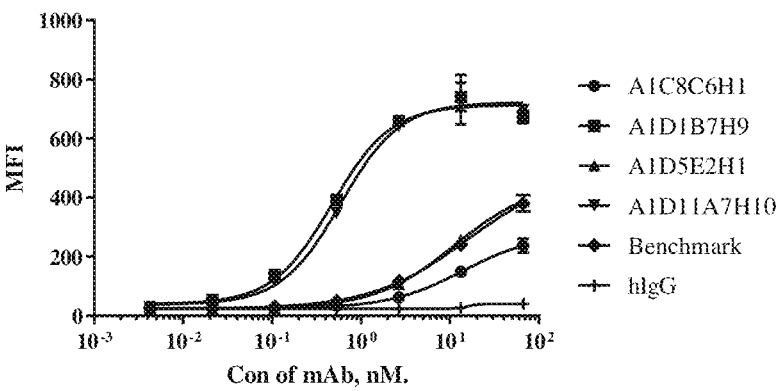
FIGS. 2A-2C show the binding capacities of antibodies A1C8C6H1, A1D1B7H9, A1D5E2H1 and A1D11A7H10 (A), A1E7G5D1, A1E10G7H9, A2A1D2F1 and A2A5C7E8 (B), A2A6B1C2, A2G4C8G7 and A2H5F1A1 (C) to human-siglec15-2D3-1E1 cells expressing human Siglec15 in a cell based binding FACS assay.
Figure 2B:
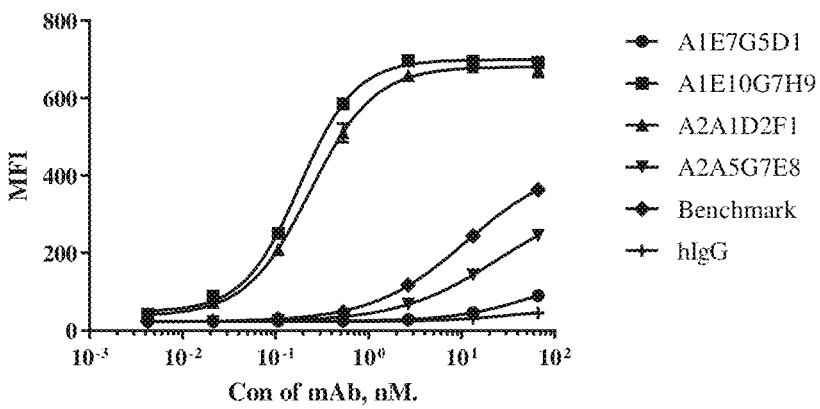
Figure 2C:
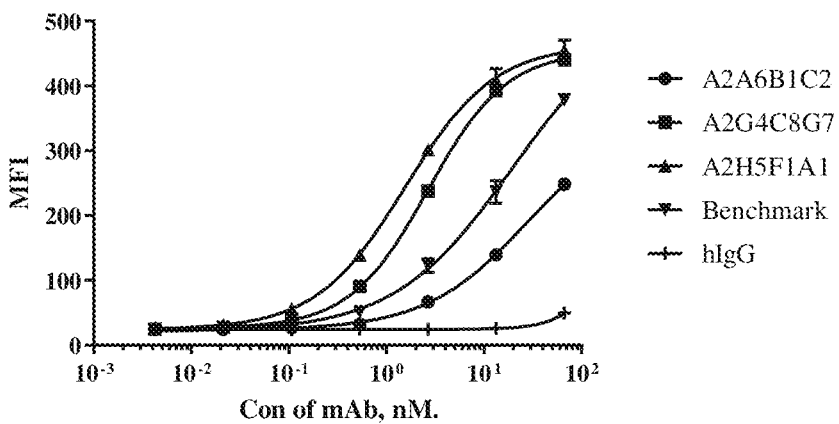

As shown in FIGS. 2A-2C, the anti-Siglec15 antibodies A1D1B7H9, A1D11A7H10, A1E10G7H9, A2A1D2F1, A2G4C8G7 and A2H5F1A1 bound to cell surface human Siglec15 more efficiently (with lower EC$_{50}$) with higher Bmax as compared with the benchmark.

Figure 3A:
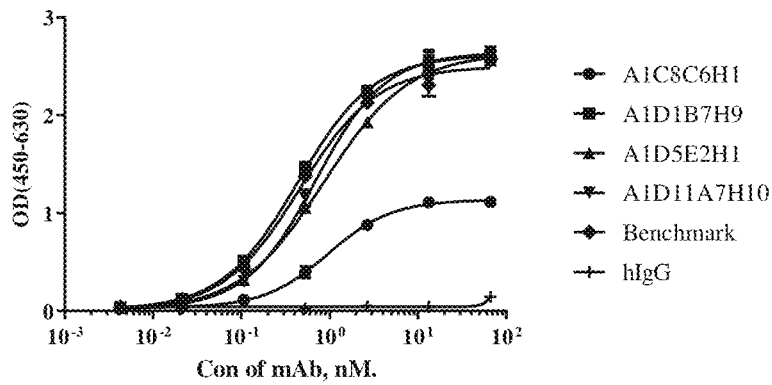
FIGS. 3A-3C show the binding capacities of antibodies A1C8C6H1, A1D1B7H9, A1D5E2H1 and A1D11A7H10 (A), A1E7G5D1, A1E10G7H9, A2A1D2F1 and A2A5C7E8 (B), A2A6B1C2, A2G4C8G7 and A2H5F1A1 (C) to cynomolgus Siglec15 in an indirect ELISA.
Figure 3B:
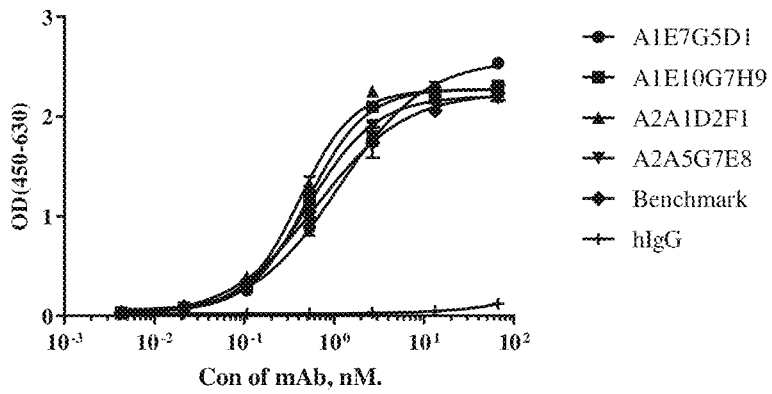
Figure 3C:
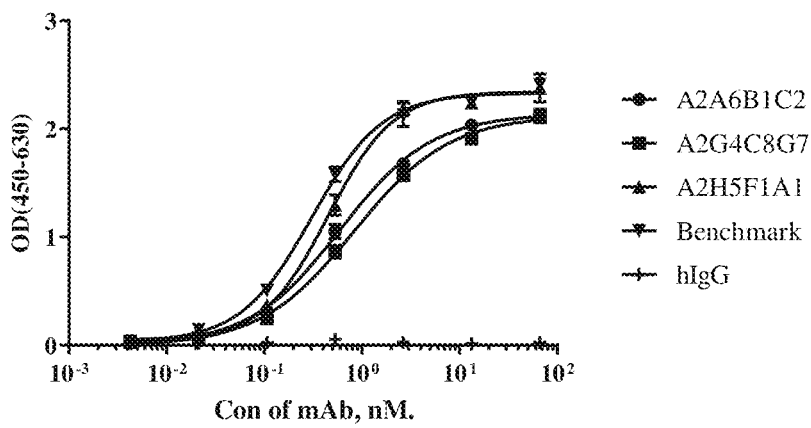
Figure 4A:
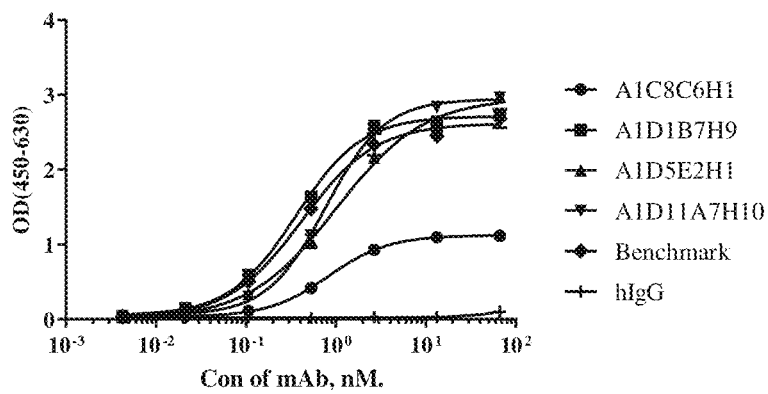
FIGS. 4A-4C show the binding capacities of antibodies A1C8C6H1, A1D1B7H9, A1D5E2H1 and A1D11A7H10 (A), A1E7G5D1, A1E10G7H9, A2A1D2F1 and A2A5C7E8
Figure 4B:
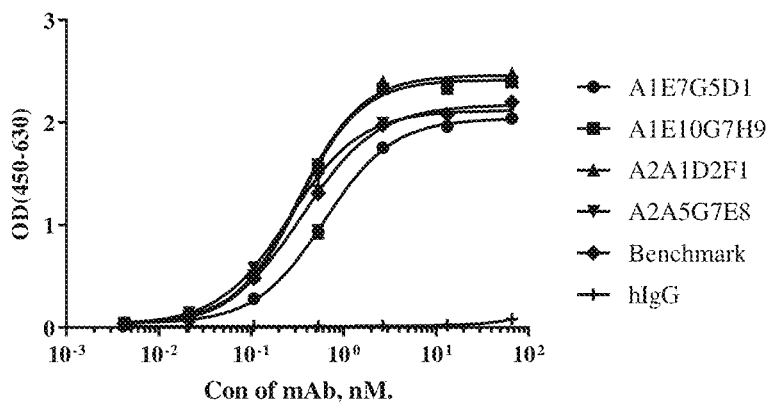
Figure 4C:
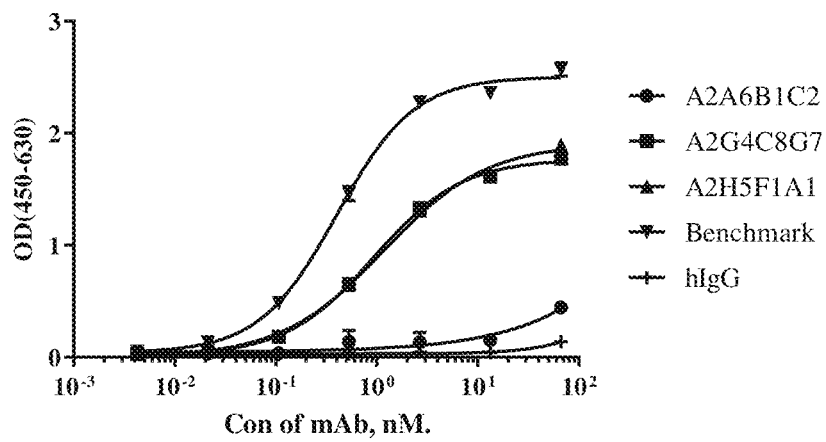

FIGS. 3A-3C showed that most of the antibodies of the disclosure bound to cynomolgus monkey Siglec15 protein with similar binding activity as compared with the benchmark. While only a few antibodies of the disclosure showed similar or better binding activity to mouse Siglec15, as shown in FIGS. 4A-4C. For example, the antibodies A1E10G7H9 and A2A1D2F1 showed higher Bmax than the benchmark.

Example 4 Blocking Activities of Anti-Siglec15 Antibodies on Siglec15-LRRC4C or Siglec15-Benchmark Binding 4.1 Ligand Blocking ELISA The activities of the anti-Siglec15 antibodies of the disclosure to block Siglec15-LRRC4C binding were measured in a competitive ELISA assay. LRRC4C is a ligand of Siglec15 and may be expressed by cancer cells (WO2018057735). Briefly, 100 μl human Siglec15-Fc protein (prepared in-house with amino acid of SEQ ID NO: 19) were coated on 96-well micro plates at 2 μg/mL in carbonate/bicarbonate buffer for 2 hours at 37° C. Plates were washed once with wash buffer (PBS+0.05% v/v Tween®-20, PBST), and blocked with 5% w/v non-fatty milk in PBST overnight at 4° C. Plates were then washed 4 times using wash buffer.

Serially diluted anti-Siglec15 antibodies or the controls (starting at 66.67 nM with a 5-fold serial dilution) in PBST with 2.5% w/v non-fatty milk were added to the Siglec15-Fc bound plates, 100 µl per well, and incubated with the human Siglec15-Fc protein at 37° C. for 40 minutes. Plates were washed 4 times again using wash buffer, then added and incubated for 40 minutes at 37° C. with 100 µl/well 290 ng/ml biotin-labeled human LRRC4C-Fc protein (prepared in-house with SEQ ID NO: 23). Plates were washed again using wash buffer. Thereafter, the plates were added with 100 µl/well streptavidin conjugated HRP (1:5000 dilution in PBST buffer, Jackson Immunoresearch, Cat #016-030-084) and incubated for 40 minutes at 37° C. Plates were washed again using wash buffer. Finally, TMB was added and the reaction was stopped using 1M $H_2SO_4$, and the absorbance of each well was read on a microplate reader using dual wavelength mode with 450 nm for TMB and 630 nm as the reference wavelength, then the OD (450-630) values were plotted against antibody concentration. Data was analyzed using GraphPad Prism software and $IC_{50}$ values were reported.

4.2 Benchmark Blocking ELISA

The abilities of the anti-Siglec15 antibodies of the disclosure to block benchmark-human Siglec15 binding were measured in a competitive ELISA assay. Briefly, the benchmark was coated on 96-well micro plates at 2 µg/mL in PBS, 100 µl per well, and incubated for 2 hours at 37° C. Then plates were washed once with wash buffer, and blocked with 5% w/v non-fatty milk in PBST overnight at 4° C. The next day, the anti-Siglec15 antibodies of the disclosure or controls were diluted with biotin labeled human Siglec15-Fc protein (prepared in-house with SEQ ID NO: 19, 37 ng/ml in PBST with 2.5% w/v non-fatty milk), starting at 80 nM with a 4-fold serial dilution, and incubated at room temperature for 40 minutes. After plate washing 4 times, the antibody/Siglec15-Fc mixtures were added to benchmark coated plates, 100 µl per well. After incubation at 37° C. for 40 minutes, plates were washed 4 times again using wash buffer. Then the plates were added and incubated with 100 µl/well streptavidin conjugated HRP for 40 minutes at 37° C. Plates were washed again using wash buffer. Finally, TMB was added and the reaction was stopped using 1M $H_2SO_4$, and the absorbance of each well was read on a microplate reader using dual wavelength mode with 450 nm for TMB and 630 nm as the reference wavelength, then the OD (450-630) values were plotted against antibody concentration. Data was analyzed using GraphPad Prism software and $IC_{50}$ values were reported.

4.3 Cell-Based Ligand-Blocking FACS

The activities of the anti-Siglec15 antibodies to block binding of Siglec15 protein to cell surface LRRC4C were evaluated by Flow Cytometry (FACS), using in house made LRRC4C-3F12-1B9 cells. Briefly, HEK-293 cells (ATCC®#CRL-1573) were transfected with pCMV-T-P plasmid constructs with the nucleotide sequence encoding human LRRC4C (amino acid residues Met1-Ile640 of uniprot #Q9HCJ2) inserted between EcoRI and XbaI following the instruction of Lipofectamine™ 3000 transfection reagent (Thermo Fisher). A stable cell named LRRC4C-3F12-1B9 was chosen for subsequent cell based ligand-blocking assay.

Briefly, the anti-Siglec15 antibodies of the disclosure or controls were diluted with human Siglec15-mouse Fc protein (prepared in-house with SEQ ID NO: 26, 8 µg/ml nM in FACS buffer), starting at 66.67 nM with a 5-fold serial dilution, and incubated at room temperature for 40 minutes. Then, LRRC4C-3F12-1B9 cells were harvested from cell culture flasks, washed twice and re-suspended in PBS containing 2% v/v Fetal Bovine Serum (FACS buffer). Then, $1 \times 10^5$ cells per well in 96 well-plates were incubated in 100 µL of the antibody/Siglec15-mouse Fc mixtures for 40 minutes at 4° C. The plates were washed twice with FACS buffer, and then added and incubated for 40 minutes at 4° C. in dark with 100 µl/well R-Phycoerythrin AffiniPure F(ab)$_2$ Fragment Goat Anti-Mouse IgG (H+L) (1:1000 dilution in FACS buffer, Jackson Immunoresearch, Cat #115-116-146). Cells were washed twice and re-suspended in FACS buffer. Fluorescence was measured using a Becton Dickinson FACSCanto II™-HTS equipment. Data was analyzed using GraphPad Prism software and $IC_{50}$ values were reported.

The results of the three assays were FIGS. 5A-5C to 7A-7C.

It can be seen from FIGS. 5A-5C that all anti-Siglec15 antibodies of the disclosure were capable of blocking human Siglec15-human LRRC4C binding, and the blocking activities were similar or lower than that of the benchmark.

FIGS. 6A-6C showed that the antibodies A1E7G5D1, A2A5C7E8, A2G4C8G7 and A2H5F1A1 were able to block human Siglec15-benchmark binding, suggesting they bound to the same or similar epitope as the benchmark did. The antibodies A1C8C6H1, A1D1B7H9, A1D5E2H1, A1D11A7H10, A1E10G7H9, A2A1D2F1 and A2A6B1C2 were unable to block human Siglec15 binding to benchmark, suggesting that A1C8C6H1, A1D1B7H9, A1D5E2H1, A1D11A7H10, A1E10G7H9, A2A1D2F1 and A2A6B1C2 might bind to different epitopes as compared to the benchmark.

Further, as shown in FIGS. 7A-7C, all anti-Siglec15 antibodies of the disclosure were capable of blocking binding of human Siglec15 to cell surface human LRRC4C with mouse Fc, with similar or lower blocking activities than the benchmark.

Example 5 Thermal Stability of Anti-Siglec 15 Antibodies

The anti-Siglec15 antibodies were also tested for their thermal stabilities. Briefly, a protein thermal shift assay was used to determine Tm (melting temperature) using a Glo-Melt™ Thermal Shift Protein Stability Kit (Biotium, Cat #33022-T). Then, the GloMelt™ dye was allowed to thaw and reach room temperature. The vial containing the dye was vortexed and centrifuged. Then, 10× dye was prepared by adding 5 µL 200× dye to 95 µL PBS. 2 µL 10× dye and 10 µg antibodies were added, and PBS was added to a total reaction volume of 20 µL. The tubes containing the dye and antibodies were briefly spun and placed in real-time PCR thermocycler (Roche, LightCycler® 480 II) set up with a melt curve program having the parameters in Table 3.

TABLE 3

Parameters for Melt Curve Program

| Profile step | Temperature | Ramp rate | Holding Time |
| --- | --- | --- | --- |
| Initial hold | 25° C. | NA | 30 s |
| Melt curve | 25-99° C. | 0.1° C./s | NA |

The melting temperatures of the antibodies of the disclosure were summarized in Table 4, suggesting that the antibodies of the disclosure were probably stable in human body.

TABLE 4

Melting temperatures of anti-Siglec15 antibodies

| Clone ID# | Tm (melting temperature) ° C. | Clone ID# | Tm (melting temperature) ° C. |
|---|---|---|---|
| A1E7G5D1 | 64.0 | A2A5C7E8 | 67.5 |
| A1C8C6H1 | 63.0 | A2H5F1A1 | 75.5 |
| A1D11A7H10 | 67.5 | A1E10G7H9 | 73.0 |
| A2A1D2F1 | 66.5 | A2G4C8G7 | 71.0 |
| A2A6B1C2 | 70.0 | A1D1B7H9 | 69.5 |
| A1D5E2H1 | 76.0 | Benchmark | 71.0 |

Example 6 Anti-Siglec15 Antibodies Reversed Siglec15-Mediated T Cell Suppression Anti-CD3 monoclonal antibodies (OKT3) (eBioscience Inc., Cat #16-0037-85) were coated on 96-well micro plates at 50 ng/mL in DPBS, 100 µl per well, overnight at 4° C. The next day, the unbound anti-CD3 monoclonal antibodies were aspirated immediately prior to PBMC addition.

Total PBMCs from a healthy human donor were washed with RPMI-1640 medium (Gibco, Cat #A10491-01) supplemented with 10% FBS (Gibco, Cat #10099-141) and centrifuged at 200 g for 15 minutes to remove the supernatant. Then, PBMC cells were labeled with 0.5 µM CFSE (Invitrogen, Cat #C1157) for 20 minutes on ice and the final cell density was $1 \times 10^6$ cells/mL. The cells were added with four times volume of RPMI-1640 medium supplemented with 10% FBS and incubated for 5 minutes at room temperature. Plates were centrifuged at 300 g for 10 minutes, and cells were re-suspended in RPMI-1640 medium supplemented with 10% FBS at a density of $6 \times 10^6$ cells/mL. Meanwhile, serially diluted anti-Siglec15 antibodies of the disclosure or controls (4-fold dilution in RPMI-1640 medium supplemented with 10% FBS, starting at 120 µg/ml) were mixed with human Siglec15-Fc protein (prepared in-house with SEQ ID NO: 19, 40 µg/ml in RPMI-1640 medium supplemented with 10% FBS) at 1:1 volume ratio, and incubated at room temperature for 30 minutes. Then, 50 µL medium containing PMBC cells and 50 µl antibody/Siglec15-Fc mixtures were added to the anti-CD3 bound plates, and incubated in a CO$_2$ incubator at 37° C. for 3 days. Then, 100 µL FACS buffer was added into each well, the cells were pipetted several times and transferred to U-shaped plates. The U-shaped plates were centrifuged to remove the supernatants. And then, the cells were incubated for 15 minutes at 4° C. in dark with 50 µl/well HFCR (1:10 dilution in FACS buffer, Biolegend Inc, Cat #422302). Cells were stained with anti-CD4 (Biolegend Inc., Cat #357410) and anti-CD8 (Biolegend Inc., Cat #301066) fluorescent mAbs (1:10 dilution in FACS buffer) for 30 minutes at 4° C. Cells were washed twice in FACS buffer (200 µL/well) and re-suspended in FACS buffer (200 µL/well). Fluorescence was measured using a Becton Dickinson FACSCanto II™-HTS equipment. Data was analyzed using GraphPad Prism software and $EC_{50}$ values were reported.

The results are shown in FIGS. 8A and 8B.

It can be seen that antibodies A2A5C7E8 and A1E10G7H9 were able to reverse Siglec15 mediated CD8$^+$ T cell and CD4$^+$ T cell suppression, at higher $EC_{50}$ compared to the benchmark. Notably, the antibody A2A5C7E8 at high doses was more efficacious than the benchmark in reversing T cell suppression, resulting in higher CD4$^+$ and CD8$^+$ T cell proliferation percentages.

Example 7 Sequencing of Anti-Siglec15 Antibodies

Two antibodies A2A5C7E8 and A1E10G7H9 were sequenced, and complete heavy chain and light chain variable region sequences and constant region sequences were obtained. The sequence ID NOs of the heavy chain and light chain variable regions were listed in Table 1, and the isotype of the heavy/light chain were determined by sequence alignment in database.

Example 8 Genetic Engineering of Anti-Siglec15 Antibody A2A5C7E8

To avoid or reduce post translational modifications such as deamidation and isomerization of certain amino acid residues in e.g., the CDR regions that might adversely affect antibody's production, stability, safety and/or efficacy, the antibody A2A5C7E8 (also referred to as A2A5C7E8-1 herein after) was further modified in the heavy chain CDR2 region. A total of 2 modified variants, namely A2A5C7E8-2 and A2A5C7E8-3, were obtained, whose CDR and heavy/light chain variable region sequence ID numbers were listed in Table 1.

The vectors each containing a nucleotide encoding the heavy chain variable region of A2A5C7E8-2 or A2A5C7E8-3 linked to human IgG1 heavy-chain constant region (SEQ ID NO: 17), and the vectors each containing a nucleotide encoding the light chain variable region linked to human kappa light-chain constant region (SEQ ID NO: 18) were transiently transfected into 50 ml of 293F suspension cell cultures in a ratio of 1.1:1 light to heavy chain construct, with 1 mg/mL PEI.

Example 9 Characterization of Modified A2A5C7E8 Variants

The modified variants A2A5C7E8-2 and A2A5C7E8-3 were purified as described above and tested in BiaCore™, Capture ELISA, Indirect ELISA, Cell-based binding FACS, Competitive ELISA and Cell-based functional assay, following the protocols of the foregoing Examples with or without modifications and also protocols described below.

For the BiaCore™ test measuring the binding affinities of the modified A2A5C7E8 variants to mouse Siglec 15, mouse Siglec15-his protein (in house made with SEQ ID NO: 22) was used.

In the T cell suppression reversion test, the A2A5C7E8 variants of the disclosure or controls at the concentration of 48 µg/ml were mixed with human Siglec15-Fc protein (SEQ ID NO: 19, 20 µg/ml in RPMI-1640 medium supplemented with 10% FBS) at 1:1 volume ratio; and the A2A5C7E8 variants or controls at the concentration of 120 µg/ml were mixed with human Siglec15-Fc protein (40 g/ml in RPMI-1640 medium supplemented with 10% FBS) at 1:1 volume ratio.

The BiaCore™ test results were summarized in Tables 5-1 and 5-2. Results of other assays were shown in FIGS. 9-14 and 15A-15D.

TABLE 5-1

Binding affinity of modified A2A5C7E8 variants to human Siglec15 and cynomolgus Siglec15

| | Kinetics on Biacore | | | | | |
|---|---|---|---|---|---|---|
| | Human Siglec15-his | | | Cynomolgus Siglec15-his | | |
| Clone ID# | $K_a$ $(M^{-1}s^{-1})$ | $K_d$ $(s^{-1})$ | $K_D$ (M) | $K_a$ $(M^{-1}s^{-1})$ | $K_d$ $(s^{-1})$ | $K_D$ (M) |
| A2A5C7E8-1 | 1.94E+06 | 7.45E−05 | 3.83E−11 | 1.13E+06 | 7.96E−05 | 7.04E−11 |
| A2A5C7E8-2 | 1.66E+06 | 2.73E−04 | 1.64E−10 | 1.14E+06 | 1.67E−04 | 1.47E−10 |
| A2A5C7E8-3 | 1.88E+06 | 7.46E−05 | 3.96E−11 | 7.08E+05 | 5.32E−05 | 7.51E−11 |
| Benchmark | 2.27E+06 | 9.55E−04 | 4.22E−10 | 1.13E+06 | 7.81E−04 | 6.88E−10 |

TABLE 5-2

Binding affinity of modified A2A5C7E8 variants to mouse Siglec15

| | Kinetics on Biacore Mouse Siglec15-his | | |
|---|---|---|---|
| Clone ID# | $K_a$ $(M^{-1}s^{-1})$ | $K_d$ $(s^{-1})$ | $K_D$ (M) |
| A2A5C7E8-1 | 2.14E+06 | 1.87E−04 | 8.75E−11 |
| A2A5C7E8-2 | 2.63E+06 | 4.95E−04 | 1.88E−10 |
| A2A5C7E8-3 | 2.24E+06 | 1.65E−04 | 7.37E−11 |
| Benchmark | 5.47E+06 | 9.31E−04 | 1.70E−10 |

As shown in Tables 5-1 and 5-2, the modified variants A2A5C7E8-2 and A2A5C7E8-3 specifically bound to human Siglec15 and cynomolgus Siglec15, with higher binding affinity than the benchmark. The antibody A2A5C7E8-3 also showed higher binding affinity to mouse Siglec15 than the benchmark. The antibody A2A5C7E8-2 showed comparable binding affinity to mouse Siglec15 as compared to the benchmark.

The modified variants A2A5C7E8-2 and A2A5C7E8-3 bound to human Siglec15 more efficiently or with higher Bmax than the benchmark, as shown in FIGS. 9 and 10, and more efficiently inhibited Siglec15-LRRC4C binding than the benchmark, as shown in FIG. 13. Further, according to FIGS. 11 and 12, modified variants A2A5C7E8-2 and A2A5C7E8-3 more efficiently bound to cynomolgus Siglec15 and mouse Siglec15 than the benchmark.

As shown in FIG. 14, the modified variants A2A5C7E8-2 and A2A5C7E8-3 were capable of blocking benchmark-Siglec15 binding, indicating that modified variants A2A5C7E8-2 and A2A5C7E8-3 bound to a similar epitope to the benchmark.

As shown in FIGS. 15A-15D, in the cell-based functional assay, the modified variants A2A5C7E8-2 and A2A5C7E8-3 reversed Siglec15 mediated CD8+ T cell and CD4+ T cell suppression, resulting in similar or higher cell proliferation percentages compared to the benchmark. Notably, when the human Siglec15-Fc protein was used at a relatively low dose, antibodies A2A5C7E8-2 and A2A5C7E8-3 were more efficacious than the benchmark in reversing CD4+ and CD8+ T cell suppression.

Example 10 Generation of Mouse Anti-Siglec15 Monoclonal Antibodies Using Hybridoma Technology Immunization, Hybridoma Fusion and Screening Mice immunization, hybridoma fusion and screening were performed according to the protocol in Example 1 with the following modifications. In specific, normal mice were used, immunizing dosages contained 50 μg recombinant human Siglec15-Fc protein per mouse per injection for primary immunization and 25 μg human Siglec15-Fc protein per mouse per injection for boost immunizations. The antigen was prepared in PBS or saline with concentration ranging from 0.25-0.67 mg/ml. A total of 50 or 25 μg antigen was injected in a volume of 150-200 μl. Each animal was immunized, and then boosted for 3 to 4 times depending on the anti-sera titer. The fused cell culture supernatant was subject to Indirect ELISA using in house made human Siglec15-his protein. Positive hybridomas secreting antibodies that bind to human Siglec15-his protein were selected and transferred to 24-well plates. These hybridomas were also subject to cell-based binding FACS, capture ELISA, indirect ELISA and ligand-blocking ELISA. Hybridoma clones producing antibodies that showed high specific human Siglec15-his binding, cynomolgus Siglec15-his binding, mouse Siglec15-his binding and human Siglec15-LRRC4C blocking activities were subcloned by limited dilution to ensure the clonality of the cell line, and then monoclonal antibodies were purified.

Example 11 Binding Affinity Determination of Mouse Anti-Siglec15 Monoclonal Antibody Using BiaCore™ Surface Plasmon Resonance The purified mouse anti-Siglec15 monoclonal antibodies generated in Example 10 were characterized for its binding affinity and binding kinetics by BiaCore™ T200 system (GE HealthCare, Pittsburgh, Pa., USA).

Briefly, goat anti-mouse IgG (GE HealthCare, Cat #BR100838, Mouse Antibody Capture Kit) was covalently linked to a CM5 chip (carboxy methyl dextran coated chip from GE HealthCare, Cat #BR100530) via primary amines using a standard amine coupling kit (GE HealthCare, Pittsburgh, Pa., USA) provided by BiaCore™. Un-reacted moieties on the biosensor surface were blocked with ethanolamine. The purified mouse anti-Siglec15 antibodies of the disclosure at the concentration of 13.3 nM, were respectively flowed onto the chip at a flow rate of 10 μL/min. Then, serially diluted human Siglec15-his protein (in house made, amino acid sequence set forth in SEQ ID NO: 20), cynomolgus monkey Siglec15-his protein (in house made, amino acid sequence set forth in SEQ ID NO: 21), or mouse Siglec15-his protein (in house made, amino acid sequence set forth in SEQ ID NO: 22), 2-fold dilution in HBS-EP+ buffer (provided by BiaCore™) starting at 80 nM, were flowed onto the chip at a flow rate of 30 μL/min. The antigen-antibody association kinetics was followed for 2 minutes and the dissociation kinetics was followed for 10 minutes. The association and dissociation curves were fit to a 1:1 Langmuir binding model using BiaCore™ evaluation software. The $K_D$, $K_a$ and $K_d$ values were determined and summarized in Tables 6-1 and 6-2 below.

TABLE 6-1

Binding affinity of mouse anti-Siglec15 antibodies to human Siglec15 and cynomolgus Siglec15

| | Kinetics on Biacore | | | | | |
|---|---|---|---|---|---|---|
| | Human Siglec15-his | | | Cynomolgus Siglec15-his | | |
| Mouse mAb ID# | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| B2D7H7A3C1 | 1.55E+06 | 5.46E−05 | 3.52E−11 | 7.11E+05 | 3.38E−04 | 4.76E−10 |
| B2G12H3E8 | 2.05E+06 | 1.76E−05 | 8.58E−12 | 9.96E+05 | 3.71E−04 | 3.72E−10 |
| B2H2H1H7 | 1.99E+06 | 3.18E−05 | 1.60E−11 | 8.69E+05 | 3.52E−04 | 4.05E−10 |

TABLE 6-2

Binding affinity of mouse anti-Siglec15 antibodies to mouse Siglec15

| | Kinetics on Biacore Mouse Siglec15 | | |
|---|---|---|---|
| Mouse mAb ID# | $K_a$ ($M^{-1}s^{-1}$) | $K_d$ ($s^{-1}$) | $K_D$ (M) |
| B2D7H7A3C1 | 1.32E+07 | 4.45E−03 | 3.37E−10 |
| B2G12H3E8 | 2.55E+07 | 1.08E−02 | 4.23E−10 |
| B2H2H1H7 | 1.89E+07 | 7.37E−03 | 3.90E−10 |

All the mouse anti-Siglec15 antibodies of the disclosure specifically bound to human Siglec15, cynomolgus monkey Siglec15 and mouse Siglec15 with high binding affinity.

Example 12 Binding Activities of Mouse Anti-Siglec15 Monoclonal Antibodies

The binding activities of mouse anti-Siglec15 antibodies to human Siglec15, cynomolgus monkey Siglec15 and mouse Siglec15 were further determined by Capture ELISA, Indirect ELISA and Flow Cytometry (FACS).

The Capture ELISA was performed following the protocol of Example 3, except that AffiniPure Goat Anti-Mouse IgG, F(ab')$_2$ fragment specific (Jackson ImmunoResearch, Cat #115-005-072) was used instead of AffiniPure Goat Anti-Human IgG F(ab')$_2$ fragment specific, 100 μl/well. The results were shown in FIG. 16.

The cell based FACS was done according to the protocol of Example 3, except that 1.5×10$^5$ cells per well in 96 well-plates were incubated in 100 μL serially diluted anti-Siglec15 antibodies or controls (starting at 66.67 nM, 5-fold serial dilution) in FACS buffer for 40 minutes on ice, and the cells were added with 100 μL R-Phycoerythrin AffiniPure F(ab')$_2$ Fragment Goat Anti-Mouse IgG (H+L) (1:1000 dilution in FACS buffer, Jackson Immunoresearch, Cat #115-116-146). The results were shown in FIG. 17.

The Indirect ELISA was done following the protocol of Example 3, except that peroxidase AffiniPure Goat Anti-Mouse IgG, Fcγ Fragment Specific, (Jackson Immunoresearch, Cat #115-035-071) was used instead of R-Phycoerythrin AffiniPure Goat Anti-Human IgG, Fcγ Fragment Specific, 100 μl/well. The results were shown in FIGS. 18 and 19.

It can be seen from FIG. 16 that the mouse anti-Siglec15 antibodies of the disclosure specifically bound to human Siglec15 with higher Bmax (maximal binding) and lower EC$_{50}$ compared to the benchmark (ch5G12, also referred to as BM, see U.S. Patent Publication No. 20190202912A1, amino acid sequences of the heavy chain and light chain set forth in SEQ ID NOs: 24 and 25, respectively), suggesting that they more efficiently bound to more human Siglec15 protein. According to FIG. 17, the mouse anti-Siglec15 antibodies of the disclosure specifically bound to cell surface human Siglec15 with a bit inferior activity in the FACS test.

FIG. 18 showed that the mouse anti-Siglec15 antibodies of the disclosure specifically bound to cynomolgus monkey Siglec15 protein with higher binding activity than the benchmark, while FIG. 19 showed that the mouse anti-Siglec15 antibodies of the disclosure specifically bound to mouse Siglec15 protein with a bit lower binding activity as compared with the benchmark.

Example 13 Blocking Activities of Mouse Anti-Siglec15 Antibodies on Siglec15-LRRC4C or Siglec15-Benchmark Binding The mouse anti-Siglec15 antibodies of the disclosure were also tested in ligand blocking ELISA and benchmark blocking ELISA following the protocols described above. The results were shown in FIGS. 20 and 21.

It can be seen from FIG. 20 that the mouse anti-Siglec15 antibodies of the disclosure were capable of blocking human Siglec15-human LRRC4C binding, and the blocking activities were a bit higher than that of the benchmark.

FIG. 21 showed that the mouse anti-Siglec15 antibodies of the disclosure were able to block human Siglec15-benchmark binding, suggesting that the mouse anti-Siglec15 antibodies of the disclosure might bind to a similar epitope as the benchmark did.

Example 14 Mouse Anti-Siglec15 Antibodies Reversed Siglec15-Mediated T Cell Suppression The mouse anti-Siglec15 antibodies of the disclosure were further tested for the bioactivities of reversing Siglec15-mediated T cell suppression following the protocol of the foregoing Example with modification and also protocol described below.

In the T cell suppression reversion test, the mouse anti-Siglec15 antibodies of the disclosure or controls at the concentration of 400 μg/ml were mixed with human Siglec15-Fc protein (SEQ ID NO: 19, 40 μg/ml in RPMI-1640 medium supplemented with 10% FBS) at 1:1 volume ratio. The results were shown in FIGS. 22A and 22B.

It can be seen that the mouse anti-Siglec15 antibodies of the disclosure were able to reverse Siglec15 mediated CD8$^+$ T cell and CD4$^+$ T cell suppression at lower or similar EC$_{50}$ compared to the benchmark, and the treatment with the antibodies of the disclosure at high doses resulted in much higher cell proliferation percentages.

The mouse antibodies of the disclosure were then sequenced, and the sequence ID numbers of the heavy/light chain variable regions were summarized in Table 1. Interestingly, the three antibodies B2D7H7A3C1, B2G12H3E8 and B2H2H1A7 had the same heavy/light chain CDR sequences.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/Sequence/SEQ ID NO. |
|---|
| VH CDR1 for A2A5C7E8, A2A5C7E8-2 and A2A5C7E8-3<br>TYWIS (SEQ ID NO: 1) |
| VH CDR2 for A2A5C7E8<br>LIDPSXISYTNYSPSFX2G (SEQ ID NO: 2) X1 = D, X2 = Q<br>LIDPSDSYTNYSPSFQG (SEQ ID NO: 44) |
| VH CDR2 for A2A5C7E8-2<br>LIDPSX1SYTNYSPSFX2G (SEQ ID NO: 2) X1 = E, X2 = Q<br>LIDPSESYTNYSPSFQG (SEQ ID NO: 45) |
| VH CDR2 for A2A5C7E8-3<br>LIDPSXISYTNYSPSFX2G (SEQ ID NO: 2) X1 = D, X2 = K<br>LIDPSDSYTNYSPSFKG (SEQ ID NO: 46) |
| VH CDR3 for A2A5C7E8, A2A5C7E8-2 and A2A5C7E8-3<br>GGYYGSEEDY (SEQ ID NO: 3) |
| VL CDR1 for A2A5C7E8, A2A5C7E8-2 and A2A5C7E8-3<br>RASQSVSSSRLA (SEQ ID NO: 4) |
| VL CDR2 for A2A5C7E8, A2A5C7E8-2 and A2A5C7E8-3<br>DASSRAT (SEQ ID NO: 5) |
| VL CDR3 for A2A5C7E8, A2A5C7E8-2 and A2A5C7E8-3<br>QQYGSSPRT (SEQ ID NO: 6) |
| VH for A2A5C7E8<br>EVQLVQSGAEVKKPGESLRISCKGSGYSFTTYWISWVRQMPGKGLEWMGLIDPSX1SYTNYSP<br>SFX2GHVTISTDKSISTAYLQWSSLKASDTAMYYCARGGYYGSEEDYWGQGTLVTVSS (SEQ<br>ID NO: 7) X1 = D, X2 = Q<br>EVQLVQSGAEVKKPGESLRISCKGSGYSFTTYWISWVRQMPGKGLEWMGLIDPSDSYTNYSPS<br>FQGHVTISTDKSISTAYLQWSSLKASDTAMYYCARGGYYGSEEDYWGQGTLVTVSS (SEQ ID<br>NO: 47)<br>GAAGTGCAGCTGGTGCAGTCCGGAGCAGAGGTGAAAAAGCCCGGGGAGTCTCTGAGGAT<br>CTCCTGTAAGGGTTCTGGATACAGCTTTACCACCTACTGGATCAGCTGGGTGCGCCAGATG<br>CCCGGGAAAGGCCTGGAGTGGATGGGTTTGATTGATCCTAGTGACTCTTATACCAACTAC<br>AGTCCGTCCTTCCAAGGCCACGTCACCATCTCAACTGACAAGTCCATCAGCACTGCCTAC<br>CTGCAGTGGAGCAGCCTGAAGGCCTCGGACACCGCCATGTATTACTGTGCGAGAGGGGGTT<br>ACTATGGTTCGGAAGAGGACTACTGGGGCCAGGGAACCCTGGTCACCGTCTCCTCA (SEQ<br>ID NO: 27) |
| VH for A2A5C7E8-2<br>EVQLVQSGAEVKKPGESLRISCKGSGYSFTTYWISWVRQMPGKGLEWMGLIDPSX1SYTNYSP<br>SFX2GHVTISTDKSISTAYLQWSSLKASDTAMYYCARGGYYGSEEDYWGQGTLVTVSS (SEQ<br>ID NO: 7) X1 = E, X2 = Q<br>EVQLVQSGAEVKKPGESLRISCKGSGYSFTTYWISWVRQMPGKGLEWMGLIDPSESYTNYSPS<br>FQGHVTISTDKSISTAYLQWSSLKASDTAMYYCARGGYYGSEEDYWGQGTLVTVSS (SEQ ID<br>NO: 48) |
| VH for A2A5C7E8-3<br>EVQLVQSGAEVKKPGESLRISCKGSGYSFTTYWISWVRQMPGKGLEWMGLIDPSX1SYTNYSP<br>SFX2GHVTISTDKSISTAYLQWSSLKASDTAMYYCARGGYYGSEEDYWGQGTLVTVSS (SEQ<br>ID NO: 7) X1 = D, X2 = K<br>EVQLVQSGAEVKKPGESLRISCKGSGYSFTTYWISWVRQMPGKGLEWMGLIDPSDSYTNYSPS<br>FKGHVTISTDKSISTAYLQWSSLKASDTAMYYCARGGYYGSEEDYWGQGTLVTVSS (SEQ ID<br>NO: 49) |
| VL for A2A5C7E8, A2A5C7E8-2 and A2A5C7E8-3<br>EIVLTQSPGTLSLSPGERATLSCRASQSVSSSRLAWFQQKSGQAPRLLIFDASSRATGIPDRFSGS<br>GSGTDFTLTISRLEPEDFAVYYCQQYGSSPRTFGQGTKVEFK (SEQ ID NO: 8)<br>GAAATTGTGTTGACGCAGTCTCCAGGCACCCTGTCTTTGTCTCCAGGGGAAAGAGCCACCC<br>TCTCCTGCAGGGCCAGTCAGAGTGTTAGCAGCAGCCGGTTAGCCTGGTTCCAGCAGAAAT<br>CTGGCCAGGCTCCCAGACTCCTCATCTTTGATGCATCCAGCAGGGCCACTGGCATCCCAGA<br>CAGGTTCAGTGGCAGTGGGTCTGGGACAGACTTCACTCTCACCATCAGCAGACTGGAGCC<br>TGAAGATTTTGCAGTGTATTACTGTCAGCAGTATGGTAGCTCACCTCGGACGTTCGGCCAA |

| Description/Sequence/SEQ ID NO. |
|---|
| GGGACCAAGGTGGAATTCAAA (SEQ ID NO: 28) |
| |
| VH CDR1 for A1E10G7H9<br>SSNWWH (SEQ ID NO: 9) |
| |
| VH CDR2 for A1E10G7H9<br>EIYHSGNTNYKPSLKS (SEQ ID NO: 10) |
| |
| VH CDR3 for A1E10G7H9<br>DEGNGWSNAFDI (SEQ ID NO: 11) |
| |
| VL CDR1 for A1E10G7H9<br>RASQSVSSSYLA (SEQ ID NO: 12) |
| |
| VL CDR2 for A1E10G7H9<br>GASGGAT (SEQ ID NO: 13) |
| |
| VL CDR3 for A1E10G7H9<br>QQYGSSPIT (SEQ ID NO: 14) |
| |
| VH for A1E10G7H9<br>QVQLQESGPGLVKPSGTLSLTCAVSGGSISSSNWWHWVRQPPGKGLEWIGEIYHSGNTNYKPS<br>LKSRVTISVDKSKNQFSLKLSSVTAADTAVYYCARDEGNGWSNAFDIWGQGTMVTVSS (SEQ<br>ID NO: 15)<br>CAGGTGCAGCTGCAGGAGTCGGGCCCAGGACTGGTGAAGCCTTCGGGGACCCTGTCCCTC<br>ACCTGCGCTGTCTCTGGTGGCTCCATCAGCAGTAGTAACTGGTGGCATTGGGTCCGCCAGC<br>CCCCAGGGAAGGGGCTGGAGTGGATTGGGGAAATCTATCATAGTGGGAACACCAACTAC<br>AAACCGTCCCTCAAGAGTCGAGTCACCATATCAGTGGACAAGTCCAAGAACCAGTTCTCC<br>CTGAAGCTGAGCTCTGTGACCGCCGCGGACACGGCCGTCTATTATTGTGCGAGAGACGAG<br>GGCAATGGCTGGTCCAATGCTTTTGATATCTGGGGCCAAGGGACAATGGTCACCGTCTCTT<br>CA (SEQ ID NO: 29) |
| |
| VLfor A1E10G7H9<br>ENVLTQSPGTLSLSPGERVTLSCRASQSVSSSYLAWYQQKPGQAPRFLIYGASGGATGIPDRFS<br>GSGSGTDFTLTISRLEPEDFAVYYCQQYGSSPITFGQGTRLEIK (SEQ ID NO: 16)<br>GAAAATGTGTTGACGCAGTCTCCAGGCACCCTGTCTCTGTCTCCAGGGGAAAGAGTCACC<br>CTCTCCTGCAGGGCCAGTCAGAGTGTTAGCAGCAGCTACTTAGCCTGGTATCAGCAGAAA<br>CCTGGCCAGGCTCCCAGGTTCCTCATCTATGGTGCATCCGGCGGGGCCACTGGCATCCCAG<br>ACAGGTTCAGTGGCAGTGGGTCTGGGACAGACTTCACTCTCACCATCAGCAGACTGGAGC<br>CTGAAGATTTTGCAGTGTATTACTGTCAGCAGTATGGTAGCTCACCGATCACCTTCGGCCA<br>AGGGACACGACTGGAGATTAAA (SEQ ID NO: 30) |
| |
| Heavy chain constant region<br>ASTKGPSVFPLAPSSKSTSGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEAL<br>HNHYTQKSLSLSPGK (SEQ ID NO: 17)<br>GCCTCCACCAAGGGCCCATCGGTCTTCCCCCTGGCACCCTCCTCCAAGAGCACCTCTGGGG<br>GCACAGCGGCCCTGGGCTGCCTGGTCAAGGACTACTTCCCCGAACCGGTGACGGTGTCGT<br>GGAACTCAGGCGCCCTGACCAGCGGCGTGCACACCTTCCCGGCTGTCCTACAGTCCTCAG<br>GACTCTACTCCCTCAGCAGCGTGGTGACCGTGCCCTCCAGCAGCTTGGGCACCCAGACCTA<br>CATCTGCAACGTGAATCACAAGCCCAGCAACACCAAGGTGGACAAGAAAGTTGAGCCCA<br>AATCTTGTGACAAAACTCACACATGCCCACCGTGCCCAGCACCTGAACTCCTGGGGGGAC<br>CGTCAGTCTTCCTCTTCCCCCCAAAACCCAAGGACACCCTCATGATCTCCCGGACCCCTGA<br>GGTCACATGCGTGGTGGTGGACGTGAGCCACGAAGACCCTGAGGTCAAGTTCAACTGGTA<br>CGTGGACGGCGTGGAGGTGCATAATGCCAAGACAAAGCCGCGGGAGGAGCAGTACAACA<br>GCACGTACCGGGTGGTCAGCGTCCTCACCGTCCTGCACCAGGACTGGCTGAATGGCAAGG<br>AGTACAAGTGCAAGGTCTCCAACAAAGCCCTCCCAGCCCCCATCGAGAAAACCATCTCCA<br>AAGCCAAAGGGCAGCCCCGAGAACCACAGGTGTACACCCTGCCCCCATCCCGGGATGAGC<br>TGACCAAGAACCAGGTCAGCCTGACCTGCCTGGTCAAAGGCTTCTATCCCAGCGACATCG<br>CCGTGGAGTGGGAGAGCAATGGGCAGCCGGAGAACAACTACAAGACCACGCCTCCCGTG<br>CTGGACTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACTACACG<br>CAGAAGAGCCTCTCCCTGTCTCCGGGTAAATGA (SEQ ID NO: 31) |
| |
| Light chain constant region<br>RTVAAPSVFIFPPSDEQLKSGTASVVCLLNNFYPREAKVQWKVDNALQSGNSQESVTEQDSKD<br>STYSLSSTLTLSKADYEKHKVYACEVTHQGLSSPVTKSFNRGEC (SEQ ID NO: 18)<br>CGTACGGTGGCTGCACCATCTGTCTTCATCTTCCCGCCATCTGATGAGCAGTTGAAATCTG<br>GAACTGCCTCTGTTGTGTGCCTGCTGAATAACTTCTATCCCAGAGAGGCCAAAGTACAGTG<br>GAAGGTGGATAACGCCCTCCAATCGGGTAACTCCCAGGAGAGTGTCACAGAGCAGGACA<br>GCAAGGACAGCACCTACAGCCTCAGCAGCACCCTGACGCTGAGCAAAGCAGACTACGAG<br>AAACACAAAGTCTACGCCTGCGAAGTCACCCATCAGGGCCTGAGCTCGCCCGTCACAAAG<br>AGCTTCAACAGGGGAGAGTGTTAG (SEQ ID NO: 32) |

| Description/Sequence/SEQ ID NO. |
| --- |
| Human Siglec15-Fc<br>MGWSCIILFLVATATGVHSFVRTKIDTTENLLNTEVHSSPAQRWSMQVPPEVSAEAGDAAVLP<br>CTFTHPHRHYDGPLTAIWRAGEPYAGPQVFRCAAARGSELCQTALSLHGRFRLLGNPRRNDLS<br>LRVERLALADDRRYFCRVEFAGDVHDRYESRHGVRLHVTAAPRIVNISVLPSPAHAFRALCTA<br>EGEPPPALAWSGPALGNSLAAVRSPREGHGHLVTAELPALTHDGRYTCTAANSLGRSEASVY<br>LFRFHGASGASTENLYFQGEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTVLHQDWLNGKEYKC<br>KVSNKALPAPIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKSLSLSPGK<br>(SEQ ID NO: 19) |
| Human Siglec15-his<br>MGWSCIILFLVATATGVHSFVRTKIDTTENLLNTEVHSSPAQRWSMQVPPEVSAEAGDAAVLP<br>CTFTHPHRHYDGPLTAIWRAGEPYAGPQVFRCAAARGSELCQTALSLHGRFRLLGNPRRNDLS<br>LRVERLALADDRRYFCRVEFAGDVHDRYESRHGVRLHVTAAPRIVNISVLPSPAHAFRALCTA<br>EGEPPPALAWSGPALGNSLAAVRSPREGHGHLVTAELPALTHDGRYTCTAANSLGRSEASVY<br>LFRFHGASGASTHHHHHHHH (SEQ ID NO: 20) |
| Cynomolgus Siglec15-his<br>MGWSCIILFLVATATGVHSFVRTKIDTTENLLNTEVHSSPAQRWSMQVPAEVSAAAGDAAVL<br>PCTFTHPHRHYDGPLTAIWRAGEPYAGPQVFRCAAARGSELCQTALSLHGRFRLLGNPRRNDL<br>SLRVERLALADDRRYFCRVEFAGDVHDRYESRHGVRLHVTAAPRIINISVLPGPAHAFRALCT<br>AEGEPPPALAWSGPALGNSAAVPSSGQGHGHLVTAELPALNHDGRYTCTAANSLGRSEASV<br>YLFRFHGASGASTHHHHHHHH (SEQ ID NO: 21) |
| Mouse Siglec15-his<br>MGWSCIILFLVATATGVHSRRDASGDLLNTEAHSAPAQRWSMQVPAEVNAEAGDAAVLPCTF<br>THPHRHYDGPLTAIWRSGEPYAGPQVFRCTAAPGSELCQTALSLHGRFRLLGNPRRNDLSRV<br>ERLALADSGRYFCRVEFTGDAHDRYESRHGVRLRVTAAAPRIVNISVLPGPAHAFRALCTAEG<br>EPPPALAWSGPAPGNSSAALQGQGHGYQVTAELPALTRDGRYTCTAANSLGRAEASVYLFRF<br>HGAPGTSTHHHHHHHH (SEQ ID NO: 22) |
| Human LRRC4C-Fc<br>MLNKMTLHPQQIMIGPRFNRALFDPLLVVLLALQLLVVAGLVRAQTCPSVCSCSNQFSKVICV<br>RKNLREVPDGISTNTRLLNLHENQIQIIKVNSFKHLRHLEILQLSRNHIRTIEIGAFNGLANLNTL<br>ELFDNRLTTIPNGAFVYLSKLKELWLRNNPIESIPSYAFNRIPSLRRLDLGELKRLSYISEGAFEG<br>LSNLRYLNLAMCNLREIPNLTPLIKLDELDLSGNHLSAIRPGSFQGLMHLQKLWMIQSQIQVIE<br>RNAFDNLQSLVEINLAHNNLTLLPHDLFTPLHHLERIHLHHNPWNCNCDILWLSWWIKDMAPS<br>NTACCARCNTPPNLKGRYIGELDQNYFTCYAPVIVEPPADLNVTEGMAAELKCRASTSLTSVS<br>WITPNGTVMTHGAYKVRIAVLSDGTLNFTNVTVQDTGMYTCMVSNSVGNTTASATLNVTAA<br>TTTPFSYFSTVTVETMEPSQDEARTTDNNVGPTPVVDWETTNVTTSLTPQSTRSTEKTFTIPVT<br>DINSGIPGIDEVMKTTKEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVKGFYPSDIAVEWESNGQP<br>ENNYKTTPPVLDSDGSFFLYSKLTVDKSRWQQGNVFSCSVMHEALHNHYTQKSLSLSPGK<br>(SEQ ID NO: 23) |
| Heavy chain of Siglec15-ch5G9<br>QVQLQQPGAELVKPGASVKMSCKASGYTFTSYWITWVIQRPGQGLEWIGDIYCGSDTMHYNE<br>KFKNKATLTVDTSSSTAYMQLSSLTSEDSAVYYCARWWDYGSSYDYFDYWGQGTTLTVSSA<br>STKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYNSTYRVVDSVLTV<br>LHQDWLNGKEYKCKVSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRWQQGNVFSCSVMHEAL<br>HNHYTQKSLSLSPGK (SEQ ID NO: 24) |
| Light chain of Siglec15-ch5G9<br>DIKMTQSPSSMYASLGERVTITCKASQDINSYLSWFQQKPGKSPKTLIYRANRLVDGVPSRFSG<br>SGSGQDYSLTISSLEYEDMGIYYCLQYDEFPYTFGGGTKLEIKRTVAAPSVFIFPPSDEQLKSGT<br>ASVVCLLNNFYPREAKVQWKVDNALQSGNSQESVTEQDSKDSTYSLSSTLTLSKADYEKHKV<br>YACEVTHQGLSSPVTKSFNRGEC (SEQ ID NO: 25) |
| Human Siglec15-mouse Fc<br>MGWSCIILFLVATATGVHSFVRTKIDTTENLLNTEVHSSPAQRWSMQVPPEVSAEAGDAAVLP<br>CTFTHPHRHYDGPLTAIWRAGEPYAGPQVFRCAAARGSELCQTALSLHGRFRLLGNPRRNDLS<br>LRVERLALADDRRYFCRVEFAGDVHDRYESRHGVRLHVTAAPRIVNISVLPSPAHAFRALCTA<br>EGEPPPALAWSGPALGNSLAAVRSPREGHGHLVTAELPALTHDGRYTCTAANSLGRSEASVY<br>LFRFHGASGASTENLYFQGEPRGPTIKPCPPCKCPAPNLLGGPSVFIFPPKIKDVLMISLSPIVTC<br>VVVDVSEDDPDVQISWFVNNVEVHTAQTQTHREDYNSTLRVVSALPIQHQDWMSGKEFKCK<br>VNNKDLPAPIERTISKPKGSVRAPQVYVLPPPEEEMTKKQVTLTCMVTDFMPEDIYVEWTNNG<br>KTELNYKNTEPVLDSDGSYFMYSKLRVEKKNWVERNSYSCSVVHEGLHNHHTTKSFSRTPGK<br>(SEQ ID NO: 26) |
| VH CDR1 formouse B2D7H7A3C1, B2G12H3E8 and B2H2H1A7<br>NYWIG (SEQ ID NO: 33) |

| Description/Sequence/SEQ ID NO. |
|---|
| VH CDR2 for mouse B2D7H7A3C1, B2G12H3E8 and B2H2H1H7<br>DIHPGINYTNNNEKFRG (SEQ ID NO: 34) |
| VH CDR3 for mouse B2D7H7A3C1, B2G12H3E8 and B2H2H1H7<br>VDYDYDGSYIMDY (SEQ ID NO: 35) |
| VL CDR1 for mouse B2D7H7A3C1, B2G12H3E8 and B2H2H1H7<br>RASSSVSYMY (SEQ ID NO: 36) |
| VL CDR2 for mouse B2D7H7A3C1, B2G12H3E8 and B2H2H1H7<br>ATSNLTS (SEQ ID NO: 37) |
| VL CDR3 for mouse B2D7H7A3C1, B2G12H3E8 and B2H2H1H7<br>QQWNSKPWT (SEQ ID NO: 38) |
| VH for mouse B2D7H7A3C1<br>QVQLQQSGAELVRPGTSVQMSCKAAGYTFTNYWIGWVKQRPGHGLEWVGDIHPGINYTNNN<br>EKFRGKATLTADTSSNTAYMQLRGLTSDDSAIYYCARVDYDYDGSYIMDYWGQGTSVTVSS<br>(SEQ ID NO: 39) |
| VH for mouse B2G12H3E8<br>QVQLKQSGAELVRPGTSVQMSCKAVGYTFTNYWIGWVKQRPGHGLEWVGDIHPGINYTNNN<br>EKFRGKATLTADTSSSTAYMQLRGLTSDDSAIYYCARVDYDYDGSYIMDYWGQGTSVTVSS<br>(SEQ ID NO: 40) |
| VH for mouse B2H2H1H7<br>QVQLQQSGAELVRPGTSVQMSCKAAGYTFTNYWIGWVKQRPGHGLEWVGDIHPGINYTNNN<br>EKFRGKATLTADTSSSTAYMQLRGLTSDDSAIYYCARVDYDYDGSYIMDYWGQGTSVTVSS<br>(SEQ ID NO: 41) |
| VL for mouse B2D7H7A3C1 and B2G12H3E8<br>QIVLSQSPALLSASPGEKVTMTCRASSSVSYMYWYQQKPGSSPKPWIYATSNLTSGVPARFSG<br>SGSGTSYSLTISRVEAEDAATYFCQQWNSKPWTFGGGSKLEIR (SEQ ID NO: 42) |
| VL for mouse B2H2H1H7<br>QIILSQSPALLSASPGEKVTMTCRASSSVSYMYWYQQKPGSSPKPWIYATSNLTSGVPARFSGS<br>GSGTSYSLTISRVEAEDAATYFCQQWNSKPWTFGGGSRLEIR (SEQ ID NO: 43) |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

We claim:

1. An isolated antibody that specifically binds to human Siglec15, the antibody comprising a heavy chain variable region comprising the $V_H$ CDR1 region, $V_H$ CDR2 region, and $V_H$ CDR3 region of the $V_H$ amino acid sequence of SEQ ID NO: 7; and a light chain variable region comprising the $V_L$ CDR1 region, $V_L$ CDR2 region, and $V_L$ CDR3 region of the $V_L$ amino acid sequence of SEQ ID NO: 8.

2. The isolated antibody of claim 1, wherein the $V_H$ CDR1, $V_H$ CDR2, $V_H$ CDR3, $V_L$ CDR1, $V_L$ CDR2, and $V_L$ CDR3 comprise the amino acid sequences set forth in SEQ ID NOs: 1, 2, 3, 4, 5, and 6, respectively.

3. The isolated antibody of claim 1, wherein the $V_H$ CDR1, $V_H$ CDR2, $V_H$ CDR3, $V_L$ CDR1, $V_L$ CDR2, and $V_L$ CDR3 comprise the amino acid sequences set forth in SEQ ID NOs: 1, 46, 3, 4, 5, and 6; 1, 44, 3, 4, 5, and 6; or 1, 45, 3, 4, 5, and 6, respectively.

4. The isolated antibody of claim 3, wherein the $V_H$ CDR1, $V_H$ CDR2, $V_H$ CDR3, $V_L$ CDR1, $V_L$ CDR2, and $V_L$ CDR3 comprise the amino acid sequences set forth in SEQ ID NOs: 1, 46, 3, 4, 5, and 6.

5. The isolated antibody of claim 1, wherein the heavy chain variable region comprises: an amino acid sequence having at least 85% identity to SEQ ID NO: 7; and/or the light chain variable region comprises an amino acid sequence having at least 85% identity to SEQ ID NO: 8.

6. The isolated antibody of claim 1, wherein the heavy chain variable region comprises: the amino acid sequence of SEQ ID NO: 7; and/or the light chain variable region comprises the amino acid sequence of SEQ ID NO: 8.

7. The isolated antibody of claim 1, wherein the heavy chain variable region and light chain variable region comprise the amino acid sequences set forth in SEQ ID NOs: 49 and 8; 48 and 8; or 47 and 8, respectively.

8. The isolated antibody of claim 7, wherein the heavy chain variable region and light chain variable region comprise the amino acid sequences set forth in SEQ ID NOs: 49 and 8, respectively.

9. The isolated antibody of claim 1, comprising a heavy chain constant region comprising the amino acid sequence of SEQ ID NO: 17 linked to the heavy chain variable region, and/or a light chain constant region comprising the amino acid sequence of SEQ ID NO: 18 linked to the light chain variable region.

10. The isolated antibody of claim 1, wherein the antibody is an IgG1, IgG2 or IgG4 isotype.

11. The isolated antibody of claim 1, wherein the antibody is a mouse, human, chimeric, or humanized antibody.

12. The isolated antibody of claim 1, wherein the antibody is conjugated to a cytotoxic agent, toxin, or radioisotope.

13. An isolated antibody that specifically binds to human Siglec15, the antibody comprising a heavy chain variable region comprising the amino acid sequence of SEQ ID NO: 7, and a light chain variable region comprising the amino acid sequence of SEQ ID NO: 8.

14. The isolated antibody of claim 13, comprising a heavy chain constant region comprising the amino acid sequence of SEQ ID NO: 17 linked to the heavy chain variable region, and/or a light chain constant region comprising the amino acid sequence of SEQ ID NO: 18 linked to the light chain variable region.

15. The isolated antibody of claim 13, wherein the antibody is an IgG1, IgG2 or IgG4 isotype.

16. An isolated antibody that specifically binds to human Siglec15, the antibody comprising: a heavy chain comprising a heavy chain variable region comprising the amino acid sequence of SEQ ID NO: 49, 48, or 47, and a heavy chain constant region having the amino acid sequence of SEQ ID NO: 17; and a light chain comprising a light chain variable region comprising the amino acid sequence of SEQ ID NO: 8, and a light chain constant region comprising the amino acid sequence of SEQ ID NO: 18.

17. The isolated antibody of claim 16, wherein the heavy chain variable region comprises the amino acid sequence of SEQ ID NO: 49.

18. A polynucleotide encoding the heavy chain variable region, and/or the light chain variable region of the antibody of claim 1.

19. A polynucleotide encoding the heavy chain, and/or the light chain of the antibody of claim 16.

20. A vector comprising the polynucleotide of claim 18.

21. A vector comprising the polynucleotide of claim 19.

22. A host cell comprising the polynucleotide of claim 18.

23. A host cell comprising:
(a) a first polynucleotide encoding an antibody heavy chain comprising a heavy chain variable region having the amino acid sequence of SEQ ID NO: 7 and a heavy chain constant region having the amino acid sequence of SEQ ID NO: 17; and (b) a second polynucleotide encoding an antibody light chain comprising a light chain variable region having the amino acid sequence of SEQ ID NO: 8 and a light chain constant region having the amino acid sequence of SEQ ID NO: 18.

24. The host cell of claim 23, wherein the first and/or the second polynucleotide are comprised in a vector.

25. A method of producing an antibody, the method comprising culturing the host cell of claim 22 under suitable conditions so that the polynucleotide is expressed and the antibody is produced.

26. A method of producing an antibody, the method comprising culturing the host cell of claim 23 under suitable conditions so that the polynucleotide is expressed and the antibody is produced.

27. A method of producing an antibody, the method comprising culturing the host cell of claim 24 under suitable conditions so that the polynucleotide is expressed and the antibody is produced.

28. A composition comprising the antibody of claim 1 and a pharmaceutically acceptable excipient.

29. A composition comprising the antibody of claim 13 and a pharmaceutically acceptable excipient.

30. A composition comprising the antibody of claim 16 and a pharmaceutically acceptable excipient.

* * * * *

SEQUENCE LISTING

```
Sequence total quantity: 50
SEQ ID NO: 1              moltype = AA  length = 5
FEATURE                   Location/Qualifiers
source                    1..5
                          mol_type = protein
                          organism = synthetic construct
SEQUENCE: 1
TYWIS                                                                   5

SEQ ID NO: 2              moltype = AA  length = 17
FEATURE                   Location/Qualifiers
VARIANT                   6
                          note = Xaa is Asp or Glu
VARIANT                   16
                          note = Xaa is Gln or Lys
source                    1..17
                          mol_type = protein
                          organism = synthetic construct
SEQUENCE: 2
LIDPSXSYTN YSPSFXG                                                      17

SEQ ID NO: 3              moltype = AA  length = 10
FEATURE                   Location/Qualifiers
REGION                    1..10
                          note = VH CDR3 for A2A5C7E8, A2A5C7E8-2 and A2A5C7E8-3
source                    1..10
                          mol_type = protein
                          organism = synthetic construct
SEQUENCE: 3
```

```
                                        GGYYGSEEDY                                                  10

SEQ ID NO: 4            moltype = AA   length = 12
FEATURE                 Location/Qualifiers
REGION                  1..12
                        note = VL CDR1 for A2A5C7E8, A2A5C7E8-2 and A2A5C7E8-3
source                  1..12
                        mol_type = protein
                        organism = synthetic construct
SEQUENCE: 4
RASQSVSSSR LA                                                                                       12

SEQ ID NO: 5            moltype = AA   length = 7
FEATURE                 Location/Qualifiers
REGION                  1..7
                        note = VL CDR2 for A2A5C7E8, A2A5C7E8-2 and A2A5C7E8-3
source                  1..7
                        mol_type = protein
                        organism = synthetic construct
SEQUENCE: 5
DASSRAT                                                                                             7

SEQ ID NO: 6            moltype = AA   length = 9
FEATURE                 Location/Qualifiers
REGION                  1..9
                        note = VL CDR3 for A2A5C7E8, A2A5C7E8-2 and A2A5C7E8-3
source                  1..9
                        mol_type = protein
                        organism = synthetic construct
SEQUENCE: 6
QQYGSSPRT                                                                                           9

SEQ ID NO: 7            moltype = AA   length = 119
FEATURE                 Location/Qualifiers
REGION                  1..119
                        note = VH for A2A5C7E8, A2A5C7E8-2 and A2A5C7E8-3
VARIANT                 55
                        note = Xaa is Asp or Glu
VARIANT                 65
                        note = Xaa is Gln or Lys
source                  1..119
                        mol_type = protein
                        organism = synthetic construct
SEQUENCE: 7
EVQLVQSGAE VKKPGESLRI SCKGSGYSFT TYWISWVRQM PGKGLEWMGL IDPSXSYTNY                   60
SPSFXGHVTI STDKSISTAY LQWSSLKASD TAMYYCARGG YYGSEEDYWG QGTLVTVSS                    119

SEQ ID NO: 8            moltype = AA   length = 108
FEATURE                 Location/Qualifiers
REGION                  1..108
                        note = VL for A2A5C7E8, A2A5C7E8-2 and A2A5C7E8-3
source                  1..108
                        mol_type = protein
                        organism = synthetic construct
SEQUENCE: 8
EIVLTQSPGT LSLSPGERAT LSCRASQSVS SSRLAWFQQK SGQAPRLLIF DASSRATGIP                   60
DRFSGSGSGT DFTLTISRLE PEDFAVYYCQ QYGSSPRTFG QGTKVEFK                               108

SEQ ID NO: 9            moltype = AA   length = 6
FEATURE                 Location/Qualifiers
REGION                  1..6
                        note = VH CDR1 for A1E10G7H9
source                  1..6
                        mol_type = protein
                        organism = synthetic construct
SEQUENCE: 9
SSNWWH                                                                                              6

SEQ ID NO: 10           moltype = AA   length = 16
FEATURE                 Location/Qualifiers
REGION                  1..16
                        note = VH CDR2 for A1E10G7H9
source                  1..16
                        mol_type = protein
                        organism = synthetic construct
SEQUENCE: 10
EIYHSGNTNY KPSLKS                                                                                   16

SEQ ID NO: 11           moltype = AA   length = 12
```

```
FEATURE                 Location/Qualifiers
REGION                  1..12
                        note = VH CDR3 for A1E10G7H9
source                  1..12
                        mol_type = protein
                        organism = synthetic construct
SEQUENCE: 11
DEGNGWSNAF DI                                                            12

SEQ ID NO: 12           moltype = AA   length = 12
FEATURE                 Location/Qualifiers
REGION                  1..12
                        note = VL CDR1 for A1E10G7H9
source                  1..12
                        mol_type = protein
                        organism = synthetic construct
SEQUENCE: 12
RASQSVSSSY LA                                                            12

SEQ ID NO: 13           moltype = AA   length = 7
FEATURE                 Location/Qualifiers
REGION                  1..7
                        note = VL CDR2 for A1E10G7H9
source                  1..7
                        mol_type = protein
                        organism = synthetic construct
SEQUENCE: 13
GASGGAT                                                                   7

SEQ ID NO: 14           moltype = AA   length = 9
FEATURE                 Location/Qualifiers
REGION                  1..9
                        note = VL CDR3 for A1E10G7H9
source                  1..9
                        mol_type = protein
                        organism = synthetic construct
SEQUENCE: 14
QQYGSSPIT                                                                 9

SEQ ID NO: 15           moltype = AA   length = 121
FEATURE                 Location/Qualifiers
REGION                  1..121
                        note = VH for A1E10G7H9
source                  1..121
                        mol_type = protein
                        organism = synthetic construct
SEQUENCE: 15
QVQLQESGPG LVKPSGTLSL TCAVSGGSIS SSNWWHWVRQ PPGKGLEWIG EIYHSGNTNY         60
KPSLKSRVTI SVDKSKNQFS LKLSSVTAAD TAVYYCARDE GNGWSNAFDI WGQGTMVTVS        120
S                                                                       121

SEQ ID NO: 16           moltype = AA   length = 108
FEATURE                 Location/Qualifiers
REGION                  1..108
                        note = VL for A1E10G7H9
source                  1..108
                        mol_type = protein
                        organism = synthetic construct
SEQUENCE: 16
ENVLTQSPGT LSLSPGERVT LSCRASQSVS SSYLAWYQQK PGQAPRFLIY GASGGATGIP         60
DRFSGSGSGT DFTLTISRLE PEDFAVYYCQ QYGSSPITFG QGTRLEIK                    108

SEQ ID NO: 17           moltype = AA   length = 330
FEATURE                 Location/Qualifiers
REGION                  1..330
                        note = Heavy chain constant region
source                  1..330
                        mol_type = protein
                        organism = synthetic construct
SEQUENCE: 17
ASTKGPSVFP LAPSSKSTSG GTAALGCLVK DYFPEPVTVS WNSGALTSGV HTFPAVLQSS         60
GLYSLSSVVT VPSSSLGTQT YICNVNHKPS NTKVDKKVEP KSCDKTHTCP PCPAPELLGG        120
PSVFLFPPKP KDTLMISRTP EVTCVVVDVS HEDPEVKFNW YVDGVEVHNA KTKPREEQYN        180
STYRVVSVLT VLHQDWLNGK EYKCKVSNKA LPAPIEKTIS KAKGQPREPQ VYTLPPSRDE        240
LTKNQVSLTC LVKGFYPSDI AVEWESNGQP ENNYKTTPPV LDSDGSFFLY SKLTVDKSRW        300
QQGNVFSCSV MHEALHNHYT QKSLSLSPGK                                        330

SEQ ID NO: 18           moltype = AA   length = 107
FEATURE                 Location/Qualifiers
```

| | | |
|---|---|---|
| REGION | 1..107 | |
| | note = Light chain constant region | |
| source | 1..107 | |
| | mol_type = protein | |
| | organism = synthetic construct | |

SEQUENCE: 18
```
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC               107
```

| | | |
|---|---|---|
| SEQ ID NO: 19 | moltype = AA   length = 502 | |
| FEATURE | Location/Qualifiers | |
| REGION | 1..502 | |
| | note = Human Siglec15-Fc | |
| source | 1..502 | |
| | mol_type = protein | |
| | organism = synthetic construct | |

SEQUENCE: 19
```
MGWSCIILFL VATATGVHSF VRTKIDTTEN LLNTEVHSSP AQRWSMQVPP EVSAEAGDAA   60
VLPCTFTHPH RHYDGPLTAI WRAGEPYAGP QVFRCAAARG SELCQTALSL HGRFRLLGNP  120
RRNDLSLRVE RLALADDRRY FCRVEFAGDV HDRYESRHGV RLHVTAAPRI VNISVLPSPA  180
HAFRALCTAE GEPPPALAWS GPALGNSLAA VRSPREGHGH LVTAELPALT HDGRYTCTAA  240
NSLGRSEASV YLFRFHGASG ASTENLYFQG EPKSCDKTHT CPPCPAPELL GGPSVFLFPP  300
KPKDTLMISR TPEVTCVVVD VSHEDPEVKF NWYVDGVEVH NAKTKPREEQ YNSTYRVVSV  360
LTVLHQDWLN GKEYKCKVSN KALPAPIEKT ISKAKGQPRE PQVYTLPPSR EEMTKNQVSL  420
TCLVKGFYPS DIAVEWESNG QPENNYKTTP PVLDSDGSFF LYSKLTVDKS RWQQGNVFSC  480
SVMHEALHNH YTQKSLSLSP GK                                          502
```

| | | |
|---|---|---|
| SEQ ID NO: 20 | moltype = AA   length = 271 | |
| FEATURE | Location/Qualifiers | |
| REGION | 1..271 | |
| | note = Human Siglec15-his | |
| source | 1..271 | |
| | mol_type = protein | |
| | organism = synthetic construct | |

SEQUENCE: 20
```
MGWSCIILFL VATATGVHSF VRTKIDTTEN LLNTEVHSSP AQRWSMQVPP EVSAEAGDAA   60
VLPCTFTHPH RHYDGPLTAI WRAGEPYAGP QVFRCAAARG SELCQTALSL HGRFRLLGNP  120
RRNDLSLRVE RLALADDRRY FCRVEFAGDV HDRYESRHGV RLHVTAAPRI VNISVLPSPA  180
HAFRALCTAE GEPPPALAWS GPALGNSLAA VRSPREGHGH LVTAELPALT HDGRYTCTAA  240
NSLGRSEASV YLFRFHGASG ASTHHHHHHH H                                271
```

| | | |
|---|---|---|
| SEQ ID NO: 21 | moltype = AA   length = 271 | |
| FEATURE | Location/Qualifiers | |
| REGION | 1..271 | |
| | note = Cynomolgus Siglec15-his | |
| source | 1..271 | |
| | mol_type = protein | |
| | organism = synthetic construct | |

SEQUENCE: 21
```
MGWSCIILFL VATATGVHSF VRTKIDTTEN LLNTEVHSSP AQRWSMQVPA EVSAAAGDAA   60
VLPCTFTHPH RHYDGPLTAI WRAGEPYAGP QVFRCAAARG SELCQTALSL HGRFRLLGNP  120
RRNDLSLRVE RLALADDRRY FCRVEFAGDV HDRYESRHGV RLHVTAAPRI INISVLPGPA  180
HAFRALCTAE GEPPPALAWS GPALGNGSAA VPSSGQGHGH LVTAELPALN HDGRYTCTAA  240
NSLGRSEASV YLFRFHGASG ASTHHHHHHH H                                271
```

| | | |
|---|---|---|
| SEQ ID NO: 22 | moltype = AA   length = 266 | |
| FEATURE | Location/Qualifiers | |
| REGION | 1..266 | |
| | note = Mouse Siglec15-his | |
| source | 1..266 | |
| | mol_type = protein | |
| | organism = synthetic construct | |

SEQUENCE: 22
```
MGWSCIILFL VATATGVHSR RDASGDLLNT EAHSAPAQRW SMQVPAEVNA EAGDAAVLPC   60
TFTHPHRHYD GPLTAIWRSG EPYAGPQVFR CTAAPGSELC QTALSLHGRF RLLGNPRRND  120
LSLRVERLAL ADSGRYFCRV EFTGDAHDRY ESRHGVRLRV TAAAPRIVNI SVLPGPAHAF  180
RALCTAEGEP PPALAWSGPA PGNSSAALQG QGHGYQVTAE LPALTRDGRY TCTAANSLGR  240
AEASVYLFRF HGAPGTSTHH HHHHHH                                      266
```

| | | |
|---|---|---|
| SEQ ID NO: 23 | moltype = AA   length = 759 | |
| FEATURE | Location/Qualifiers | |
| REGION | 1..759 | |
| | note = Human LRRC4C-Fc | |
| source | 1..759 | |
| | mol_type = protein | |
| | organism = synthetic construct | |

SEQUENCE: 23
```
MLNKMTLHPQ QIMIGPRFNR ALFDPLLVVL LALQLLVVAG LVRAQTCPSV CSCSNQFSKV   60
ICVRKNLREV PDGISTNTRL LNLHENQIQI IKVNSFKHLR HLEILQLSRN HIRTIEIGAF  120
```

```
NGLANLNTLE  LFDNRLTTIP  NGAFVYLSKL  KELWLRNNPI  ESIPSYAFNR  IPSLRRLDLG   180
ELKRLSYISE  GAFEGLSNLR  YLNLAMCNLR  EIPNLTPLIK  LDELDLSGNH  LSAIRPGSFQ   240
GLMHLQKLWM  IQSQIQVIER  NAFDNLQSLV  EINLAHNNLT  LLPHDLFTPL  HHLERIHLHH   300
NPWNCNCDIL  WLSWWIKDMA  PSNTACCARC  NTPPNLKGRY  IGELDQNYFT  CYAPVIVEPP   360
ADLNVTEGMA  AELKCRASTS  LTSVSWITPN  GTVMTHGAYK  VRIAVLSDGT  LNFTNVTVQD   420
TGMYTCMVSN  SVGNTTASAT  LNVTAATTTP  FSYFSTVTVE  TMEPSQDEAR  TTDNNVGPTP   480
VVDWETTNVT  TSLTPQSTRS  TEKTFTIPVT  DINSGIPGID  EVMKTTKEPK  SCDKTHTCPP   540
CPAPELLGGP  SVFLFPPKPK  DTLMISRTPE  VTCVVVDVSH  EDPEVKFNWY  VDGVEVHNAK   600
TKPREEQYNS  TYRVVSVLTV  LHQDWLNGKE  YKCKVSNKAL  PAPIEKTISK  AKGQPREPQV   660
YTLPPSREEM  TKNQVSLTCL  VKGFYPSDIA  VEWESNGQPE  NNYKTTPPVL  DSDGSFFLYS   720
KLTVDKSRWQ  QGNVFSCSVM  HEALHNHYTQ  KSLSLSPGK                            759

SEQ ID NO: 24               moltype = AA  length = 452
FEATURE                     Location/Qualifiers
REGION                      1..452
                            note = Heavy chain of Siglec15-ch5G9
source                      1..452
                            mol_type = protein
                            organism = synthetic construct
SEQUENCE: 24
QVQLQQPGAE  LVKPGASVKM  SCKASGYTFT  SYWITWVIQR  PGQGLEWIGD  IYCGSDTMHY    60
NEKFKNKATL  TVDTSSSTAY  MQLSSLTSED  SAVYYCARWW  DYGSGYDFD   YWGQGTTLTV   120
SSASTKGPSV  FPLAPSSKST  SGGTAALGCL  VKDYFPEPVT  VSWNSGALTS  GVHTFPAVLQ   180
SSGLYSLSSV  VTVPSSSLGT  QTYICNVNHK  PSNTKVDKKV  EPKSCDKTHT  CPPCPAPELL   240
GGPSVFLFPP  KPKDTLMISR  TPEVTCVVVD  VSHEDPEVKF  NWYVDGVEVH  NAKTKPREEQ   300
YNSTYRVVSV  LTVLHQDWLN  GKEYKCKVSN  KALPAPIEKT  ISKAKGQPRE  PQVYTLPPSR   360
EEMTKNQVSL  TCLVKGFYPS  DIAVEWESNG  QPENNYKTTP  PVLDSDGSFF  LYSKLTVDKS   420
RWQQGNVFSC  SVMHEALHNH  YTQKSLSLSP  GK                                  452

SEQ ID NO: 25               moltype = AA  length = 214
FEATURE                     Location/Qualifiers
REGION                      1..214
                            note = Light chain of Siglec15-ch5G9
source                      1..214
                            mol_type = protein
                            organism = synthetic construct
SEQUENCE: 25
DIKMTQSPSS  MYASLGERVT  ITCKASQDIN  SYLSWFQQKP  GKSPKTLIYR  ANRLVDGVPS    60
RFSGSGSGQD  YSLTISSLEY  EDMGIYYCLQ  YDEFPYTFGG  GTKLEIKRTV  AAPSVFIFPP   120
SDEQLKSGTA  SVVCLLNNFY  PREAKVQWKV  DNALQSGNSQ  ESVTEQDSKD  STYSLSSTLT   180
LSKADYEKHK  VYACEVTHQG  LSSPVTKSFN  RGEC                                214

SEQ ID NO: 26               moltype = AA  length = 503
FEATURE                     Location/Qualifiers
REGION                      1..503
                            note = Human Siglec15-mouse Fc
source                      1..503
                            mol_type = protein
                            organism = synthetic construct
SEQUENCE: 26
MGWSCIILFL  VATATGVHSF  VRTKIDTTEN  LLNTEVHSSP  AQRWSMQVPP  EVSAEAGDAA    60
VLPCTFTHPH  RHYDGPLTAI  WRAGEPYAGP  QVFRCAAARG  SELCQTALSL  HGRFRLLGNP   120
RRNDLSLRVE  RLALADDRRY  FCRVEFAGDV  HDRYESRHGV  RLHVTAAPRI  VNISVLPSPA   180
HAFRALCTAE  GEPPPALAWS  GPALGNSLAA  VRSPREGHGH  LVTAELPALT  HDGRYTCTAA   240
NSLGRSEASV  YLFRFHGASG  ASTENLYFQG  EPRGPTIKPC  PPCKCPAPNL  LGGPSVFIFP   300
PKIKDVLMIS  LSPIVTCVVV  DVSEDDPDVQ  ISWFVNNVEV  HTAQTQTHRE  DYNSTLRVVS   360
ALPIQHQDWM  SGKEFKCKVN  NKDLPAPIER  TISKPKGSVR  APQVYVLPPP  EEEMTKKQVT   420
LTCMVTDFMP  EDIYVEWTNN  GKTELNYKNT  EPVLDSDGSY  FMYSKLRVEK  KNWVERNSYS   480
CSVVHEGLHN  HHTTKSFSRT  PGK                                             503

SEQ ID NO: 27               moltype = DNA  length = 357
FEATURE                     Location/Qualifiers
misc_feature                1..357
                            note = VH for A2A5C7E8
source                      1..357
                            mol_type = other DNA
                            organism = synthetic construct
SEQUENCE: 27
gaagtgcagc  tggtgcagtc  cggagcagag  gtgaaaaagc  ccggggagtc  tctgaggatc    60
tcctgtaagg  gttctggata  cagctttacc  acctactgga  tcagctgggt  gcgccagatg   120
cccgggaaag  gcctggagtg  gatgggtttg  attgatccta  gtgacttta   taccaactac   180
agtccgtcct  tccaaggcca  cgtcaccatc  tcaactgaca  agtccatcag  cactgcctac   240
ctgcagtgga  gcagcctgaa  ggcctcggac  accgccatgt  attactgtgc  gagaggggt   300
tactatggtt  cggaagagga  ctactggggc  cagggaaccc  tggtcaccgt  ctcctca     357

SEQ ID NO: 28               moltype = DNA  length = 324
FEATURE                     Location/Qualifiers
misc_feature                1..324
                            note = VL for A2A5C7E8, A2A5C7E8-2 and A2A5C7E8-3
```

```
source                  1..324
                        mol_type = other DNA
                        organism = synthetic construct
SEQUENCE: 28
gaaattgtgt tgacgcagtc tccaggcacc ctgtctttgt ctccagggga aagagccacc   60
ctctcctgca gggccagtca gagtgttagc agcagccggt tagcctggtt ccagcagaaa  120
tctggccagg ctcccagact cctcatcttt gatgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcacctcg gacgttcggc  300
caagggacca aggtggaatt caaa                                         324

SEQ ID NO: 29           moltype = DNA   length = 363
FEATURE                 Location/Qualifiers
misc_feature            1..363
                        note = VH for A1E10G7H9
source                  1..363
                        mol_type = other DNA
                        organism = synthetic construct
SEQUENCE: 29
caggtgcagc tgcaggagtc gggcccagga ctggtgaagc cttcggggac cctgtccctc   60
acctgcgctg tctctggtgg ctccatcagc agtagtaact ggtggcattg ggtccgccag  120
cccccaggga aggggctgga gtggattggg aaaatctatc atagtgggaa caccaactac  180
aaaccgtccc tcaagagtcg agtcaccata tcagtggaca agtccaagaa ccagttctct  240
ctgaagctga gctctgtgac cgccgcggac acggccgtct attattgtgc gagagacgag  300
ggcaatggct ggtccaatgc ttttgatatc tggggccaag ggacaatggt caccgtctct  360
tca                                                                363

SEQ ID NO: 30           moltype = DNA   length = 324
FEATURE                 Location/Qualifiers
misc_feature            1..324
                        note = VL for A1E10G7H9
source                  1..324
                        mol_type = other DNA
                        organism = synthetic construct
SEQUENCE: 30
gaaaatgtgt tgacgcagtc tccaggcacc ctgtctctgt ctccagggga aagagtcacc   60
ctctcctgca gggccagtca gagtgttagc agcagctact agcctggta tcagcagaaa  120
cctggccagg ctcccaggtt cctcatctat ggtgcatccg gcggggccac tggcatccca  180
gacaggttca gtggcagtgg gtctgggaca gacttcactc tcaccatcag cagactggag  240
cctgaagatt ttgcagtgta ttactgtcag cagtatggta gctcaccgat caccttcggc  300
caagggacac gactggagat taaa                                         324

SEQ ID NO: 31           moltype = DNA   length = 993
FEATURE                 Location/Qualifiers
misc_feature            1..993
                        note = Heavy chain constant region
source                  1..993
                        mol_type = other DNA
                        organism = synthetic construct
SEQUENCE: 31
gcctccacca agggcccatc ggtcttcccc ctggcaccct cctccaagag cacctctggg   60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctggggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gggtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag gcagccccg agaaccacag gtgtacaccc tgcccccatc ccgggatgag  720
ctgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa tga                               993

SEQ ID NO: 32           moltype = DNA   length = 324
FEATURE                 Location/Qualifiers
misc_feature            1..324
                        note = Light chain constant region
source                  1..324
                        mol_type = other DNA
                        organism = synthetic construct
SEQUENCE: 32
cgtacggtgg ctgcaccatc tgtcttcatc ttcccgccat ctgatgagca gttgaaatct   60
ggaactgcct ctgttgtgtg cctgctgaat aacttctatc ccagagaggc caaagtacag  120
tggaaggtgg ataacgcccct ccaatcgggt aactcccagg agagtgtcac agagcaggac  180
```

```
agcaaggaca gcacctacag cctcagcagc accctgacgc tgagcaaagc agactacgag    240
aaacacaaag tctacgcctg cgaagtcacc catcagggcc tgagctcgcc cgtcacaaaa    300
agcttcaaca ggggagagtg ttag                                           324
```

```
SEQ ID NO: 33           moltype = AA   length = 5
FEATURE                 Location/Qualifiers
REGION                  1..5
                        note = VH CDR1 for mouse B2D7H7A3C1, B2G12H3E8 and B2H2H1A7
source                  1..5
                        mol_type = protein
                        organism = synthetic construct
SEQUENCE: 33
NYWIG                                                                  5

SEQ ID NO: 34           moltype = AA   length = 17
FEATURE                 Location/Qualifiers
REGION                  1..17
                        note = VH CDR2 for mouse B2D7H7A3C1, B2G12H3E8 and B2H2H1H7
source                  1..17
                        mol_type = protein
                        organism = synthetic construct
SEQUENCE: 34
DIHPGINYTN NNEKFRG                                                    17

SEQ ID NO: 35           moltype = AA   length = 13
FEATURE                 Location/Qualifiers
REGION                  1..13
                        note = VH CDR3 for mouse B2D7H7A3C1, B2G12H3E8 and B2H2H1H7
source                  1..13
                        mol_type = protein
                        organism = synthetic construct
SEQUENCE: 35
VDYDYDGSYI MDY                                                        13

SEQ ID NO: 36           moltype = AA   length = 10
FEATURE                 Location/Qualifiers
REGION                  1..10
                        note = VL CDR1 for mouse B2D7H7A3C1, B2G12H3E8 and B2H2H1H7
source                  1..10
                        mol_type = protein
                        organism = synthetic construct
SEQUENCE: 36
RASSSVSYMY                                                            10

SEQ ID NO: 37           moltype = AA   length = 7
FEATURE                 Location/Qualifiers
REGION                  1..7
                        note = VL CDR2 for mouse B2D7H7A3C1, B2G12H3E8 and B2H2H1H7
source                  1..7
                        mol_type = protein
                        organism = synthetic construct
SEQUENCE: 37
ATSNLTS                                                                7

SEQ ID NO: 38           moltype = AA   length = 9
FEATURE                 Location/Qualifiers
REGION                  1..9
                        note = VL CDR3 for mouse B2D7H7A3C1, B2G12H3E8 and B2H2H1H7
source                  1..9
                        mol_type = protein
                        organism = synthetic construct
SEQUENCE: 38
QQWNSKPWT                                                              9

SEQ ID NO: 39           moltype = AA   length = 122
FEATURE                 Location/Qualifiers
REGION                  1..122
                        note = VH for mouse B2D7H7A3C1
source                  1..122
                        mol_type = protein
                        organism = synthetic construct
SEQUENCE: 39
QVQLQQSGAE LVRPGTSVQM SCKAAGYTFT NYWIGWVKQR PGHGLEWVGD IHPGINYTNN      60
NEKFRGKATL TADTSSNTAY MQLRGLTSDD SAIYYCARVD YDYDGSYIMD YWGQGTSVTV     120
SS                                                                   122

SEQ ID NO: 40           moltype = AA   length = 122
FEATURE                 Location/Qualifiers
REGION                  1..122
```

```
                        note = VH for mouse B2G12H3E8
source                  1..122
                        mol_type = protein
                        organism = synthetic construct
SEQUENCE: 40
QVQLKQSGAE LVRPGTSVQM SCKAVGYTFT NYWIGWVKQR PGHGLEWVGD IHPGINYTNN    60
NEKFRGKATL TADTSSSTAY MQLRGLTSDD SAIYYCARVD YDYDGSYIMD YWGQGTSVTV   120
SS                                                                 122

SEQ ID NO: 41           moltype = AA   length = 122
FEATURE                 Location/Qualifiers
REGION                  1..122
                        note = VH for mouse B2H2H1H7
source                  1..122
                        mol_type = protein
                        organism = synthetic construct
SEQUENCE: 41
QVQLQQSGAE LVRPGTSVQM SCKAAGYTFT NYWIGWVKQR PGHGLEWVGD IHPGINYTNN    60
NEKFRGKATL TADTSSSTAY MQLRGLTSDD SAIYYCARVD YDYDGSYIMD YWGQGTSVTV   120
SS                                                                 122

SEQ ID NO: 42           moltype = AA   length = 106
FEATURE                 Location/Qualifiers
REGION                  1..106
                        note = VL for mouse B2D7H7A3C1 and B2G12H3E8
source                  1..106
                        mol_type = protein
                        organism = synthetic construct
SEQUENCE: 42
QIVLSQSPAL LSASPGEKVT MTCRASSSVS YMYWYQQKPG SSPKPWIYAT SNLTSGVPAR    60
FSGSGSGTSY SLTISRVEAE DAATYFCQQW NSKPWTFGGG SKLEIR                 106

SEQ ID NO: 43           moltype = AA   length = 106
FEATURE                 Location/Qualifiers
REGION                  1..106
                        note = VL for mouse B2H2H1H7
source                  1..106
                        mol_type = protein
                        organism = synthetic construct
SEQUENCE: 43
QIILSQSPAL LSASPGEKVT MTCRASSSVS YMYWYQQKPG SSPKPWIYAT SNLTSGVPAR    60
FSGSGSGTSY SLTISRVEAE DAATYFCQQW NSKPWTFGGG SRLEIR                 106

SEQ ID NO: 44           moltype = AA   length = 17
FEATURE                 Location/Qualifiers
source                  1..17
                        mol_type = protein
                        organism = synthetic construct
SEQUENCE: 44
LIDPSDSYTN YSPSFQG                                                  17

SEQ ID NO: 45           moltype = AA   length = 17
FEATURE                 Location/Qualifiers
source                  1..17
                        mol_type = protein
                        organism = synthetic construct
SEQUENCE: 45
LIDPSESYTN YSPSFQG                                                  17

SEQ ID NO: 46           moltype = AA   length = 17
FEATURE                 Location/Qualifiers
source                  1..17
                        mol_type = protein
                        organism = synthetic construct
SEQUENCE: 46
LIDPSDSYTN YSPSFKG                                                  17

SEQ ID NO: 47           moltype = AA   length = 119
FEATURE                 Location/Qualifiers
source                  1..119
                        mol_type = protein
                        organism = synthetic construct
SEQUENCE: 47
EVQLVQSGAE VKKPGESLRI SCKGSGYSFT TYWISWVRQM PGKGLEWMGL IDPSDSYTNY    60
SPSFQGHVTI STDKSISTAY LQWSSLKASD TAMYYCARGG YYGSEEDYWG QGTLVTVSS   119

SEQ ID NO: 48           moltype = AA   length = 119
FEATURE                 Location/Qualifiers
source                  1..119
```

```
                        mol_type = protein
                        organism = synthetic construct
SEQUENCE: 48
EVQLVQSGAE VKKPGESLRI SCKGSGYSFT TYWISWVRQM PGKGLEWMGL IDPSESYTNY    60
SPSFQGHVTI STDKSISTAY LQWSSLKASD TAMYYCARGG YYGSEEDYWG QGTLVTVSS    119

SEQ ID NO: 49           moltype = AA  length = 119
FEATURE                 Location/Qualifiers
source                  1..119
                        mol_type = protein
                        organism = synthetic construct
SEQUENCE: 49
EVQLVQSGAE VKKPGESLRI SCKGSGYSFT TYWISWVRQM PGKGLEWMGL IDPSDSYTNY    60
SPSFKGHVTI STDKSISTAY LQWSSLKASD TAMYYCARGG YYGSEEDYWG QGTLVTVSS    119

SEQ ID NO: 50           moltype = AA  length = 15
FEATURE                 Location/Qualifiers
source                  1..15
                        mol_type = protein
                        organism = synthetic construct
SEQUENCE: 50
GGGGSGGGGS GGGGS                                                    15
```